United States Patent
Nakamura

(10) Patent No.: US 11,707,259 B2
(45) Date of Patent: Jul. 25, 2023

(54) WIRELESS NEEDLE GUIDANCE USING ENCODER SENSOR AND ENCODER SCALE TO ACHIEVE POSITIONAL SENSING BETWEEN MOVABLE COMPONENTS

(71) Applicant: CANON U.S.A., INC., Melville, NY (US)

(72) Inventor: Hitoshi Nakamura, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 735 days.

(21) Appl. No.: 16/653,761

(22) Filed: Oct. 15, 2019

(65) Prior Publication Data

US 2020/0121287 A1    Apr. 23, 2020

Related U.S. Application Data

(60) Provisional application No. 62/747,934, filed on Oct. 19, 2018.

(51) Int. Cl.
*A61B 17/34*    (2006.01)
*A61B 5/00*    (2006.01)
(Continued)

(52) U.S. Cl.
CPC .......... *A61B 8/4472* (2013.01); *A61B 5/0002* (2013.01); *A61B 5/061* (2013.01);
(Continued)

(58) Field of Classification Search
CPC ..... A61B 8/4472; A61B 5/0002; A61B 5/061; A61B 8/0841; A61B 17/3403
See application file for complete search history.

(56) References Cited

U.S. PATENT DOCUMENTS 4,608,977 A * 9/1986 Brown ................... A61B 90/11
378/162
8,774,901 B2 7/2014 Velusamy et al.
(Continued)

FOREIGN PATENT DOCUMENTS

WO    2017/010992 A1    1/2017
WO    2018/175094 A1    9/2018

OTHER PUBLICATIONS

Tokuda, J., et al., "Integrated navigation and control software system for MRI-guided robotic prostate interventions", Comput Med Imaging Graph., vol. 34, No. 1, Jan. 2010, pp. 1-15.
(Continued)

*Primary Examiner* — Serkan Akar
*Assistant Examiner* — Amal Aly Farag
(74) *Attorney, Agent, or Firm* — Canon U.S.A., Inc. I.P. Division

(57) ABSTRACT

One or more devices, systems, methods and storage mediums for performing medical procedure (e.g., needle guidance, ablation, biopsy, etc.) planning and/or performance, and/or for performing guidance of multiple probes or multiple needles, are provided. Examples of applications for such devices, systems, methods and storage mediums include imaging, evaluating and diagnosing biological objects, such as, but not limited to, lesions and tumors, and such devices, systems, methods and storage mediums may be used for radiotherapy applications (e.g., to determine whether to place seed(s) for radiotherapy). Even in instances where communication between a medical tool or needle guidance device and a system is wireless or wired, preferably guidance information is still gathered and transmitted, especially in instances where wireless or wired communication signals are intermittent or interrupted.

26 Claims, 14 Drawing Sheets

(51) Int. Cl.
*A61B 5/06* (2006.01)
*A61B 8/00* (2006.01)
*A61B 8/08* (2006.01)
*H04W 88/00* (2009.01)
*A61B 1/06* (2006.01)

(52) U.S. Cl.
CPC ........ *A61B 8/0841* (2013.01); *A61B 17/3403* (2013.01); *H04W 88/00* (2013.01); *A61B 1/0684* (2013.01)

(56) References Cited

U.S. PATENT DOCUMENTS

| | | | |
|---|---|---|---|
| 9,222,996 B2 | 12/2015 | Fujimoto et al. | |
| 9,398,936 B2 | 7/2016 | Razzaque et al. | |
| 9,521,961 B2 | 12/2016 | Silverstein et al. | |
| 9,867,673 B2 | 1/2018 | Onuma et al. | |
| 2010/0082040 A1* | 4/2010 | Sahni | A61B 90/11 606/130 |
| 2012/0226145 A1 | 9/2012 | Chang et al. | |
| 2014/0049629 A1 | 2/2014 | Siewerdsen et al. | |
| 2014/0275978 A1* | 9/2014 | Fujimoto | G01R 33/286 600/422 |
| 2016/0120610 A1 | 5/2016 | Wu | |
| 2017/0000581 A1 | 1/2017 | Tokuda et al. | |
| 2017/0000582 A1 | 1/2017 | Fleig et al. | |
| 2017/0014200 A1* | 1/2017 | Onuma | A61B 17/3403 |
| 2017/0172458 A1 | 6/2017 | Kato et al. | |
| 2018/0098819 A1 | 4/2018 | Onuma et al. | |
| 2018/0103979 A1 | 4/2018 | Arimitsu et al. | |
| 2018/0168559 A1 | 6/2018 | Hautvast et al. | |
| 2018/0228568 A1 | 8/2018 | Kato et al. | |
| 2019/0008591 A1 | 1/2019 | Desai et al. | |
| 2019/0046232 A1 | 2/2019 | Tokuda et al. | |
| 2019/0090953 A1 | 3/2019 | Nakamura | |
| 2019/0105109 A1 | 4/2019 | Kato | |
| 2019/0117317 A1 | 4/2019 | Abayazid et al. | |
| 2019/0151023 A1 | 5/2019 | Lu et al. | |
| 2019/0159844 A1 | 5/2019 | Daniels et al. | |
| 2020/0054378 A1 | 2/2020 | Kincaid et al. | |
| 2020/0121219 A1 | 4/2020 | Ganesan et al. | |
| 2020/0121392 A1 | 4/2020 | Daniels | |

OTHER PUBLICATIONS

Brattain, Laura J., et al., "Simple and Effective Ultrasound Needle Guidance System", 33rd Annual International Conference of the IEEE EMBS, Boston, Massachusetts USA, Aug. 30-Sep. 3, 2011, pp. 8090-8093 (https://biodesign.seas.harvard.edu/files/biodesignlab/files/2011_-_brattain_-_simple_and_effective_ultrasound_needle_guidance_system.pdf).

Liu, S., et al., "Automatic Multiple-Needle Surgical Planning of Robotic-Assisted Microwave Coagulation in Large Liver Tumor Therapy", Plos One, vol. 11, No. 3, Mar. 16, 2016, pp. 1-34.

Youtube DEMCON—CT compatible needle positioning system—obtained at https://www.youtube.com/watch?v=wou5-kqMsDo, published on Jun. 8, 2016.

DEMCON Website—CT compatible needle positioning system obtained at https://www.demcon.nl/en/showcase/precise-needle-positioning/; website link viewed on about or around Jul. 20, 2018; submitted screenshots obtained on Aug. 21, 2019.

Clarius—Portable Ultrasound for Interventional https://clarius.com/specialty/interventional/; website link viewed on about or around Jul. 20, 2018; submitted screenshots obtained on Aug. 21, 2019.

Civco, Tracking Brackets with Ultra-Pro™ Needle Guide, https://www.civco.com/catalog/fusion-tracking-technology/tracking-brackets-ultra-pro-needle-guide/; website link viewed on about or around Jul. 20, 2018; submitted screenshots obtained on Aug. 21, 2019.

Chenyang Xu, et al., "Gradient Vector Flow: A New External Force for Snakes", IEEE Proc. Conf. on Comp. Vis. Patt. Recog. (CVPR'97), Los Alamitos: Comp. Soc. Press, Jul. 1997, pp. 66-71.

A. Gouze, et al., "Watershed-driven Active Contours for Moving Object Segmentation", Proceedings of IEEE International Conference on Image Processing (ICIP), vol. II, Genova, Italie, Sep. 2005, pp. 818-821 (four pages in PDF file).

U.S. Appl. No. 16/539,769, filed Aug. 13, 2019.

* cited by examiner

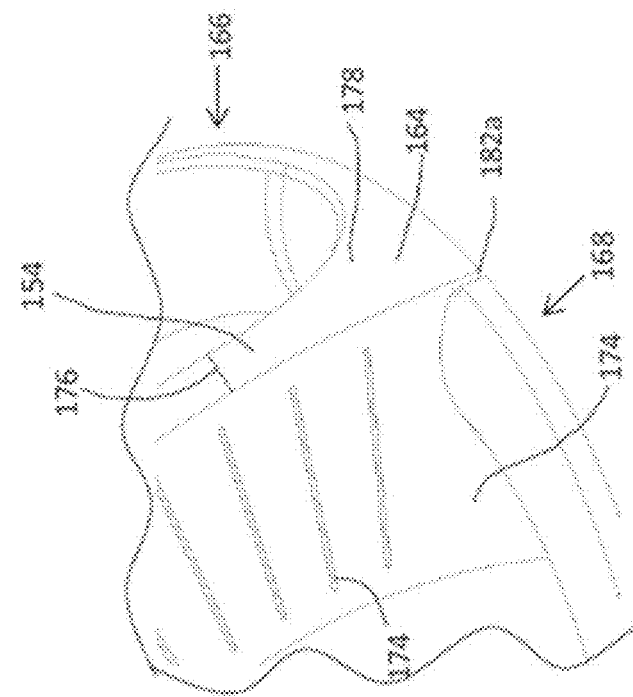
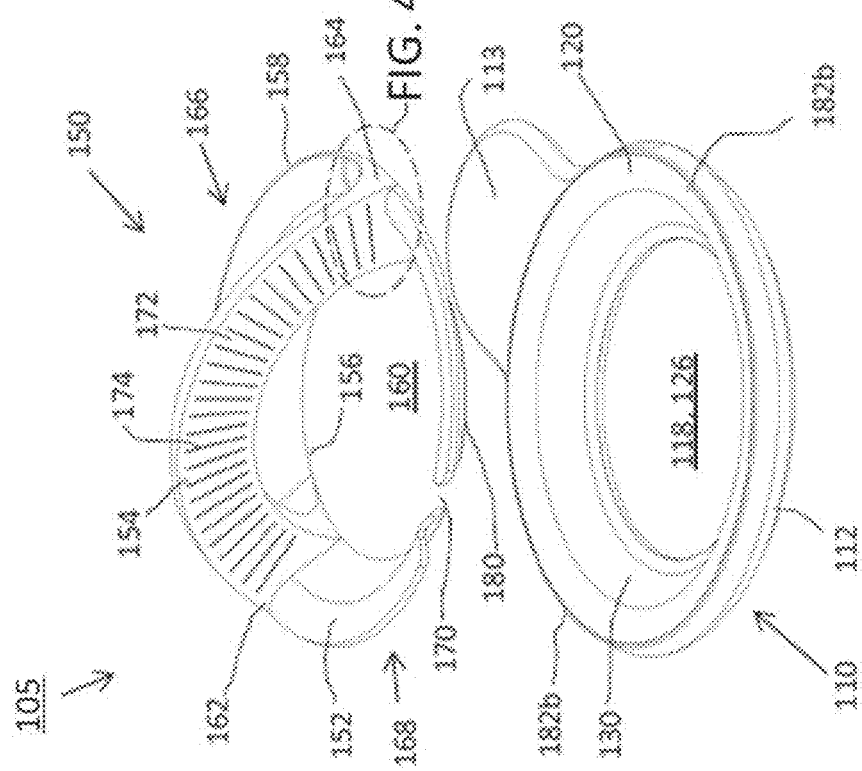
FIG. 4B
FIG. 4A

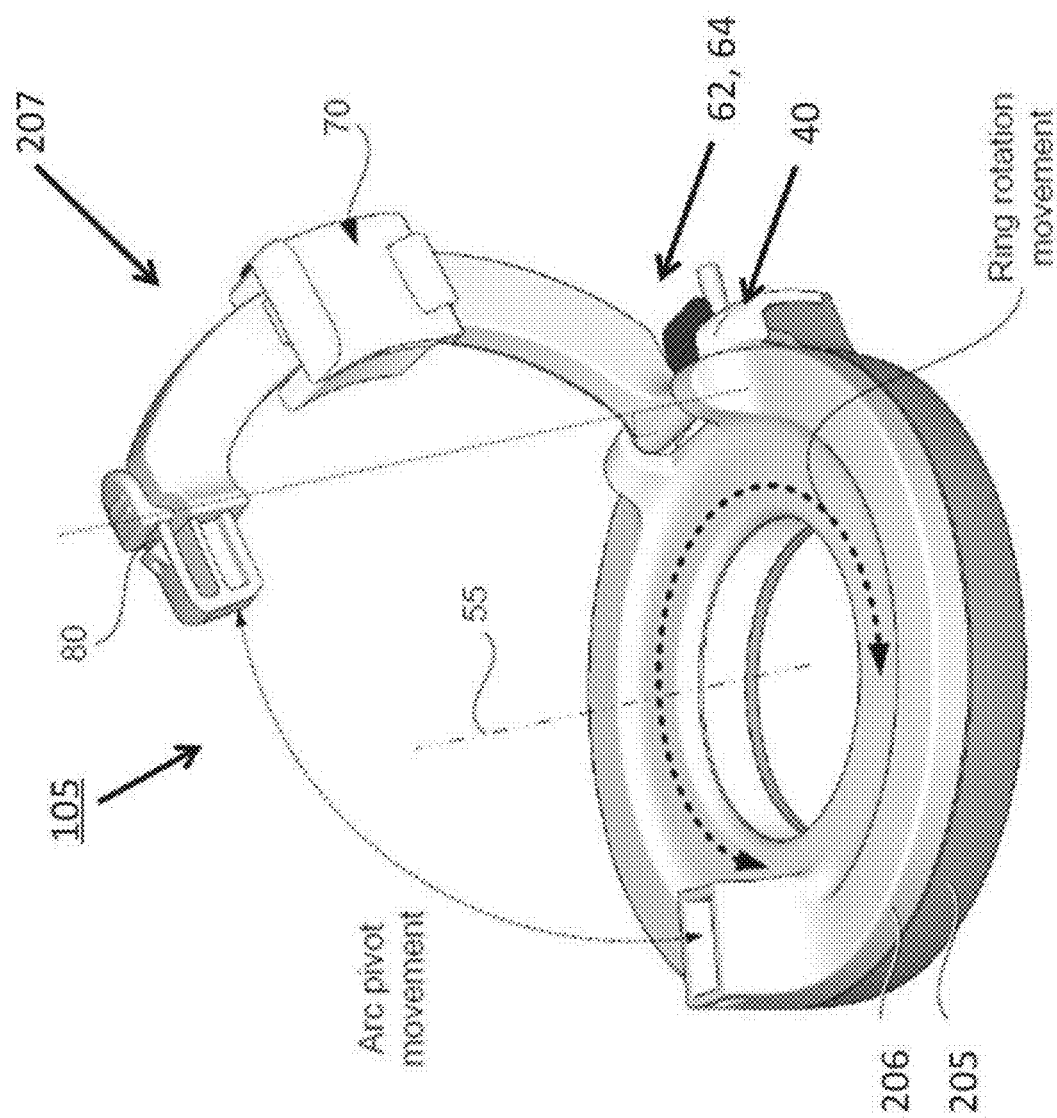

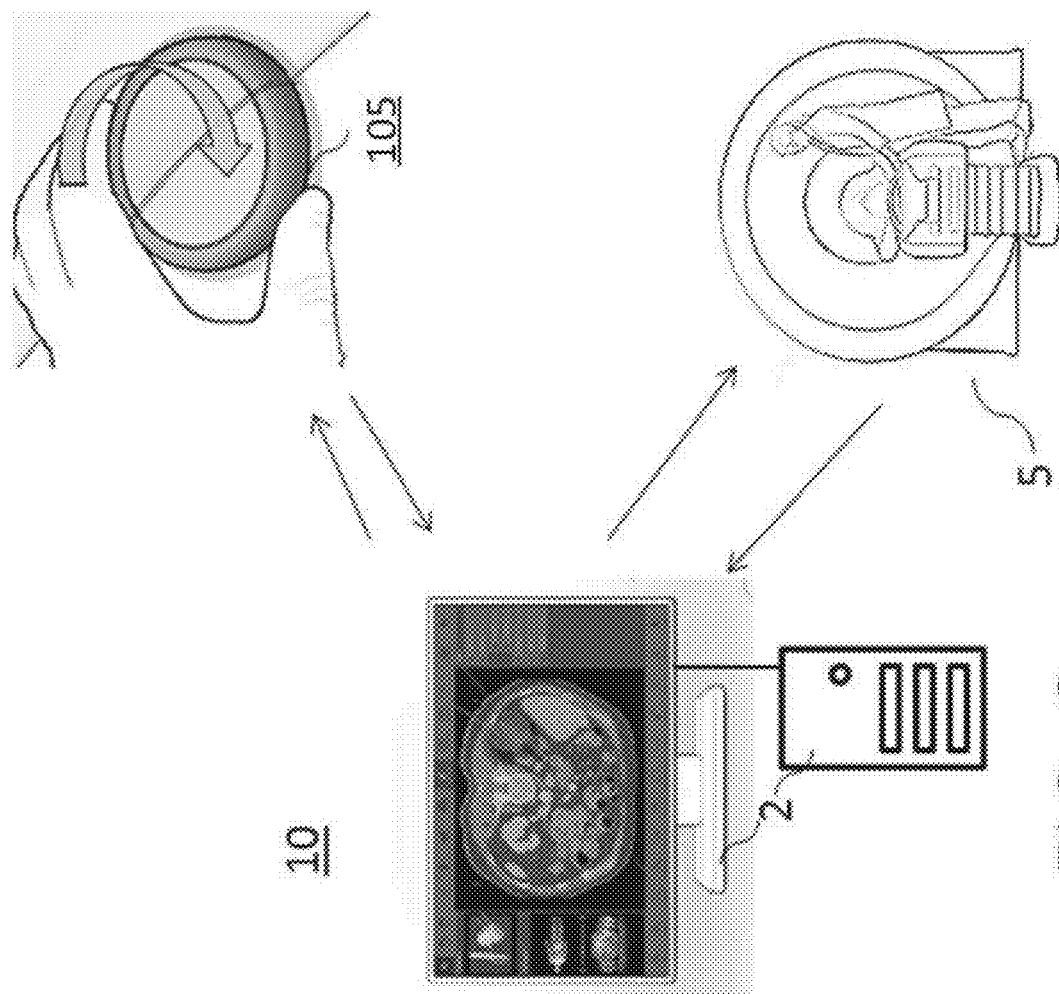
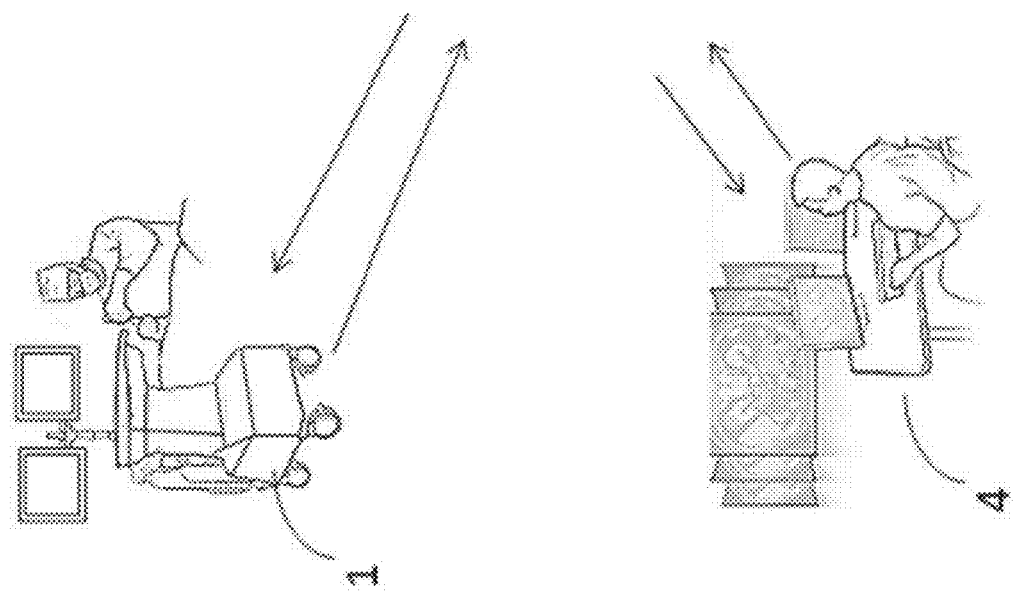
FIG. 6

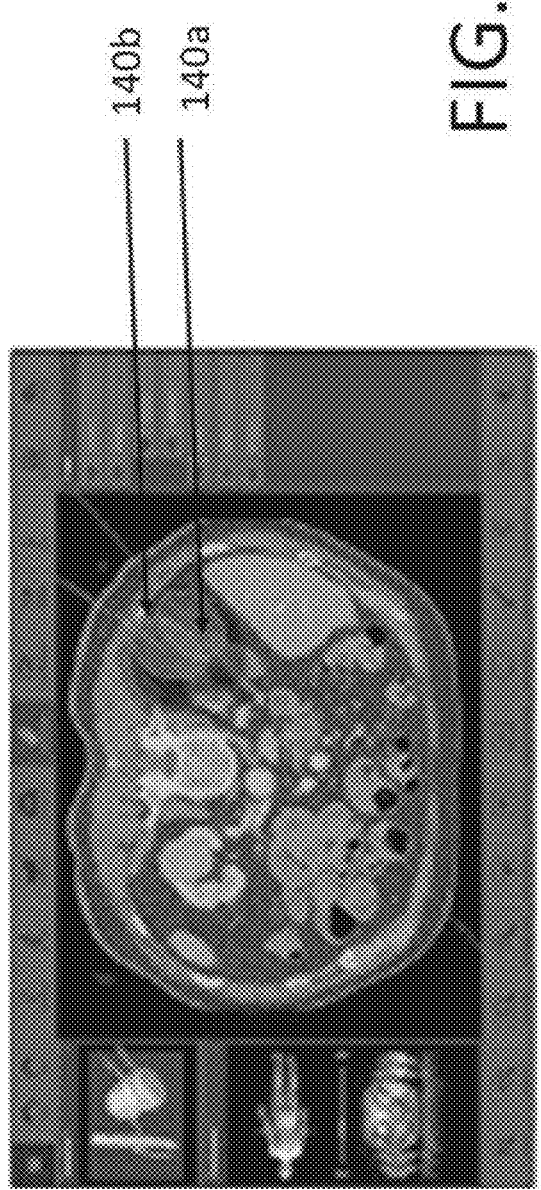
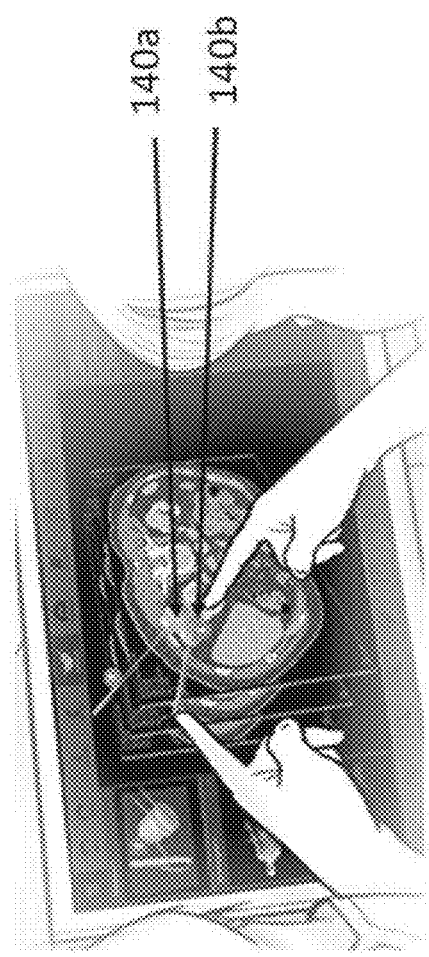
FIG. 7A
FIG. 7B

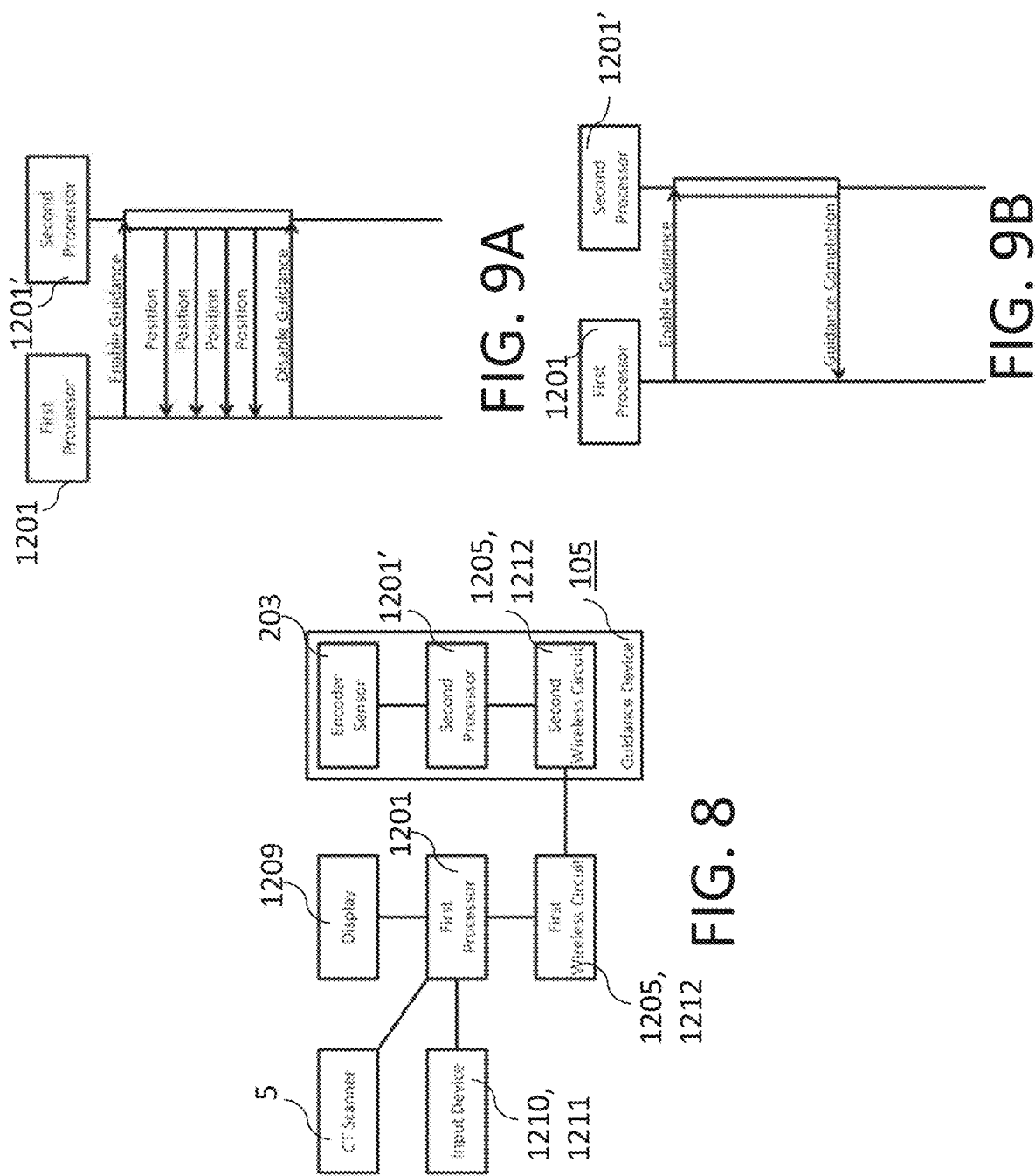

WIRELESS NEEDLE GUIDANCE USING ENCODER SENSOR AND ENCODER SCALE TO ACHIEVE POSITIONAL SENSING BETWEEN MOVABLE COMPONENTS

CROSS-REFERENCE TO RELATED APPLICATION(S)

This application relates, and claims priority, to U.S. Patent Application Ser. No. 62/747,934, filed Oct. 19, 2018, the entire disclosure of which is incorporated by reference herein in its entirety.

FIELD OF THE INVENTION

The present disclosure relates generally to the field of optical imaging, such as, but not limited to, in the field of interventional oncology, and more particularly to apparatuses, systems, methods and storage mediums for wireless guidance of one or more medical instruments, such as needles used for minimally invasive puncture treatment. Examples of ablation applications include imaging, evaluating and characterizing/identifying biological objects or tissue, such as, but not limited to, for identification, location and treatment of lesions/tumors, operation/procedure planning, simulation and ablation performance. The present disclosure also relates to wireless guiding and positioning of one or more needles in a treatment.

BACKGROUND OF THE INVENTION

Minimally invasive medical procedures are becoming increasingly popular in the medical community due to shortened hospital stays and improved quality of life for the patient. For example, in the field of interventional oncology, percutaneous ablations are often preferred over surgical resection due to the minimally invasive nature of the procedure and thus shortened patient recovery period.

There are various forms of ablation, and successful ablation requires good planning. Ablation is normally ordered after diagnosis by oncologists who decide the ablation procedure is the best to treat a lesion/tumor. An interventional radiologist (IR) may be involved to gather and analyze images to accurately characterize tumors and their size and to review results from a biopsy procedure. However, diagnostic imaging is rarely good enough to plan with, so an IR may conduct initial imaging before developing/finalizing an action plan and starting an ablation procedure. The ablation strategy may include selection of an imaging modality in the procedure, probe insertion points, a number of probes and trajectories of the insertion, a modality of ablation such as microwave, cryo, etc., patient position during the procedure, coordinating with other clinicians (e.g., anesthetist, nurses, equipment technicians, etc.), etc.

Ablation takes a lot of planning, and there are a lot of variables. For example, clinicians in ablation planning try to figure out where is the target ablation zone including a lesion/tumor, where are the critical structures/features that must be avoided during the procedure, where is the target point in the target zone, what is the entry point on the body surface so that the probe can get into the body and reach a target point(s), what is the trajectory to connect an entry point to a target point while avoiding any critical structure/feature with consideration of needle orientation when scanning the body with the needle inserted, how many probes are needed to form an ablation zone, how big and what shape the ablation zone is, etc. When a lesion/tumor is identified and an ablation zone is defined, based on ablation probe type and quantities, clinicians normally use a visual overlay of the two zones to estimate the coverage zone, which tends to be inaccurate or be a less objective measure since it is a mental visual estimate.

Even though ablation procedures are very complex, the procedure that is currently performed by clinicians is predominantly done manually and iteratively, which is error prone and may increase the time required to perform an ablation (i.e., be inefficient). Planning in particular is largely performed by clinicians with some help from basic visualization software. Clinicians typically start with reading Computed Tomography (CT) or Magnetic Resonance Imaging (MRI) scans, identify the target region and plan the insertion point and/or trajectory/orientation. For example, in at least one ablation planning scenario, clinicians load Digital Imaging and Communications in Medicine (DICOM) images of a patient into a computer and view 2D slice by slice of the CT or MRI scans of the patient. By going through the DICOM image slices, a clinician may construct a mental 3D model of internal anatomy of concern. By using the DICOM images, the clinicians may identify where the lesion/tumor is and may identify the relationship of the lesion/tumor and its surrounding critical structure, to determine the optimal probe entry point, target point and consequently the trajectory from the entry point to the target point.

Then the clinicians may identify the entry point on the surface of the body that corresponds to what the clinicians envisioned in the image scans. The clinicians may perform a test drive to insert a needle a little bit, perform a scan, and find the difference between the actual needle insertion demonstrated by the scan and what was expected before the insertion. This gives the clinicians a chance to make any correction if necessary. This step may be repeated several times for the needle to finally reach the target point.

Typically, a target point is in a center of the lesion/tumor in a case where a single probe is used. Clinicians may use a pointing device such as a mouse or touch point to mark a location in the center of the lesion/tumor which is shown in the basic visualization software. Clinicians may either place a probe tip to allow ablation to occur, or may implant seeds for radio/chemo therapy. Even the marking process is manual and approximate in nature. In 2D, marking a center position for an object may not be hard, even though many times it may not be accurate due to human visual and motor action inaccuracy/error. However, a clinician using 2D slice view to figure out a center of a 3D volume which includes a stack of 2D slices may be difficult and error prone if the center of the volume is the target point, and the clinician may be tricked by image artifacts and/or human limitation in 3D reasoning. In 3D, marking a center position is much harder because of the intricate limitation of visualization/rendering software. Relying on clinicians' intuition, experience and visual understanding to define a target point is not optimal (for reliability, repeatability, traceability, etc.), particularly in 3D space. When the lesion/tumor has a very complicated shape, defining an appropriate target is more or less an art, and it is difficult to achieve consistency.

If multiple needles are needed to make the ablation zone large enough to cover the target zone, clinicians typically use a first needle as reference, and plan the next needles based on the result from the first or previous needle insertion and/or ablation. If there are multiple needle insertions needed, cases are done mostly in an incremental fashion—for example, plan, insert a needle, scan, make an adjustment or modification to the original plan (if needed) based on the scan of the inserted needle, insert another needle, etc.

Devices/hardware is also lacking to help clinicians aid in the insertion of multiple probes or needles during a procedure, such as, but not limited to ablation, biopsy, or other procedures.

In current practice, as aforementioned, needles or other devices, such as ablation probes, are guided in a free-handed manner using medical imaging for guidance. It is very difficult to achieve these preset needle or probe configurations with this approach and thus an improved guidance method is needed. Clinicians employ incremental insertion movement by trial and error to deal with the inevitable organ movement and deformation (e.g., as aforementioned, a clinician may insert a needle a little, scan, read the image(s) to find out how much the needle is off, adjust or change the needle trajectory if needed or keep going, if the target point is moved during probe insertion, etc.). Currently, a first probe insertion is made and scanned to use the scan as a reference. Then subsequent incremental insertions of the probe may be made towards the target with scans after each insertion to assess same. Such a process may include repositioning the patient if needed to make insertion more controllable. Additionally, an IR or clinician may assume the probe is rigid and that organs have no deformation and movement from now until the insertion. Alternatively to scanning, an ultrasound transducer along with the ablation probe may be used to guide the probe into the planning direction to reach the target, which requires ultrasound image fusion with CT/MRI (CT fluoroscopy is another technique that may be used with CT during planning and performance of ablation). This not only increases the procedure time, but also wastes a lot of efforts in adjustment/making changes. Of course, it is also likely having impact(s) on or causing possible damage to nearby structure and tissues. Considering organ movement and deformation may make ablation planning and performance more complex, and may hamper interaction between clinicians and ablation planning and performance devices. The reality is that many factors (e.g., breathing, body movement or pose change, organ deformation due to interaction with the probe, etc.) affect probe insertion and may change between planned insertion and actual insertion. Such changes may also invalidate the planned insertion. Respiratory gating, or asking patients to hold their breath, is time consuming monitoring techniques that may be used to assist with insertion. Modeling organ deformation is another way to try to anticipate movement and deformation issues with insertion. However, such procedures do not guarantee success or efficiency. Ultimately, the purpose of probe insertion is to perform or conduct ablation. Once the probe is setup properly, ablation is thereafter performed.

A further complexity that arises in guiding and placing needles or probes relates to network issues. For example, network troubles may disturb navigation when a wireless connection is applied to a system or apparatus. This issue increases in complexity for iterative processes such as the iterative methods discussed above, and may result in additional room for error in a procedure when a network signal is lost or unstable.

In view of the above, there is a need for software and/or hardware to provide clinicians with help to make needle guidance, especially wireless needle guidance, easier, more efficient (e.g., reduce procedure time) and more effective (including, but not limited to, more cost-effective (cheaper), optimized for lesion/tumor removal, etc.), in addition to providing enhancement in visualization and/or needle or probe guidance/placement. There is also a need for a reliable and simple apparatus, system, method and storage medium for wireless needle guidance that provides a better (e.g., more efficient, less burden on a patient, etc.), faster (e.g., less or minimized operating time) and more objective way to guide needles and/or probes in configurations necessary for performing procedures. There is also a need for a flexible wireless system that provides a support for needle positioning and/or improved usability even in a case where a wireless connection is lost or unstable.

SUMMARY OF THE INVENTION

One or more systems, devices, methods and storage mediums are provided herein, including, but not limited to, apparatus(es), system(s) or device(s), and methods and storage mediums for guiding multiple needles or ablation probes. In the medical environment, in one or more applications, it is necessary to position a needle or multiple needles, or a probe or multiple probes, precisely inside and/or on tissue or a specific organ for accurate diagnosis or minimally invasive procedure(s), such as, but not limited to, therapy, treatment, etc.

One or more embodiments of the present disclosure relate to one or more medical devices, methods and storage mediums for holding and positioning a needle or needles, or a probe or multiple ablation probes, in desired geometric configurations, including using wireless connection(s) or communication(s) methods to achieve the desired placement(s).

One or more embodiments provide useful hardware for physically guiding planned needles along planned trajectories, including using wireless connection(s) to achieve the desired trajectories/placement(s).

In one or more embodiments, percutaneous ablation procedures involve the physician having to guide ablation probe(s) to a target of interest, such as an area of interest (e.g., a tumor, a nodule, a lesion, etc.), deep in the body with the aid of medical imaging (e.g., CT, MRI, Ultrasound, other scanning devices, etc.). Various ablation modalities exist (radiofrequency, microwave, cryo, laser, and irreversible electroporation). The physician selects the needle(s) or probe(s) which will be able to perform a desired medical procedure (e.g., fully ablate a tumor along with a safety margin surrounding the tumor to reduce the risk of tumor recurrence). In some cases, a single needle or probe may not be enough to achieve the desired procedure (such as, but not limited to, achieve full tumor coverage), and thus multiple needles or probes may be used (e.g., for a larger ablation zone to ensure full tumor coverage). Moreover, there is often a preset probe configuration that is desired in each ablation modality. For example, in microwave and irreversible electroporation a parallel probe configuration is desired. In the parallel probe configuration, probes are guided parallel at a preset maximum distance. The preset maximum distance ensures a larger uniform ablation zone. Exceeding the maximum probe distance may result in independent ablation zones around each probe and thus lead to missed tumor cells between probes causing or leading to tumor recurrence. In cryo-ablation, many physicians prefer to bracket the tumor in a conical probe arrangement in order to ensure all insertion points of the probes are in close proximity. Sharing a close insertion point for all probes in cryo-ablation is desired so that the physician can more easily protect the skin from cryo burns by applying warm saline around the probe insertion points. In one or more embodiments, drug delivery and/or treatment may also be performed in addition to one or more of biopsy, ablation, therapy (e.g., cryotherapy), aspiration, etc. One or more embodiments of the present disclosure provide configurations and processes for achieving wireless guidance and placement of needle(s) and/or probe(s) to perform a desired minimally invasive procedure(s).

In one or more embodiments, an apparatus and a method for a medical guidance device may include a base assembly including a base ring or a fixed portion having an inner circumference defining an opening, and a guide or moving portion rotateably mateable with the base assembly, the guide having a frame with an inner circumference defining an opening and an outer circumference, wherein, in a configuration where the guide is mated with the base assembly, the opening of the frame overlays the opening of the base ring. The medical guidance apparatus also has an arc member (and may, in one or more embodiments, have a holder slideably attached to the arc member, wherein the holder is configured to hold a medical tool intended to be guided by the medical guidance apparatus). Preferably, in one or more embodiments, the fiducial markers are located or disposed in the base assembly (e.g., in a base ring or fixed portion, portion attached to a patient, in the rotateably mateable guide or moveable portion, etc.).

In one or more embodiments, the arc member comprises a guidance surface, wherein the guidance surface comprises one or more angular reference marks. The angular reference marks may be used to align with an indicator configured upon the arc member guidance surface to accurately situate the holder in the desired angular position. In further embodiments, the medical guidance apparatus comprises a gap extending from the inner circumference of the frame to the outer circumference of the frame, to allow for detachment and/or reattachment of the medical guidance apparatus to the surface without interrupting the medical tool.

In additional embodiments, the holder further comprises a groove for accepting the medical tool and a door for holding the medical tool in the holder. Furthermore, the door may be hingedly attached to the holder, and further comprises a tab, configured to align with the groove on the holder, to aid in holding the medical tool in the holder. In other embodiments, the door may be removable and/or replaceable.

One or more further embodiments of the subject disclosure include a method of guiding a medical instrument, comprising, mounting a medical guidance apparatus about a predetermined insertion point of a surface, the medical guidance apparatus comprising a base assembly including a base ring having an inner circumference defining an opening and a guide rotateably mateable with the base assembly, the guide including a frame having an inner circumference defining an opening and an outer circumference, wherein, in a configuration where the guide is mated with the base assembly, the opening of the frame overlays the opening of the base ring. The apparatus may further include an arc member and a holder slideably attached to the arc member, wherein the holder is configured to hold a medical tool intended to be guided by the medical guidance apparatus. The method may further include positioning the guide to a predetermined position relative to the base ring, positioning the medical instrument to a predetermined position upon the holder, and inserting the medical instrument through the insertion point.

The present disclosure, via one or more embodiments, achieves fundamental needle or multi-needle, or probe or multi-probe, configurations desired for procedures, such as, but not limited to, ablations, biopsy, diagnosis, treatment, etc., without multiple interchangeable probe guides.

One or more other features discussed herein may reduce the risk of user error.

One or more features of one or more embodiments of the present disclosure may be used for various types of devices, such as, but not limited to, an MRI, Ultrasound or other scan devices instead of a CT scanner. One or more embodiments may be able to apply any position detectors instead of an encoder. One or more embodiments may use a speaker, vibrator or other lighting devices instead of light emitting diodes (LEDs). While ablation procedures are discussed above as one or more examples of needle guidance and placement, one or more embodiments may apply biopsy needles or other medical procedure needles instead of ablation needles.

In accordance with one or more embodiments of the present disclosure, needle guidance planning and performance apparatuses and systems, and methods and storage mediums may operate to characterize biological objects, such as, but not limited to, lesions, tumors, critical structures, etc.

In accordance with at least another aspect of the present disclosure, the ablation probe or needle placement/guidance technique(s) discussed herein may be employed to reduce the cost of at least one of manufacture and maintenance of ablation planning and performance devices, systems and storage mediums by reducing or minimizing a number of components therein to cut down cost.

According to other aspects of the present disclosure, one or more additional apparatuses, one or more systems, one or more methods, and one or more storage mediums using needle or probe wireless guidance technique(s) are discussed herein. Further features of the present disclosure will become apparent from the following description of exemplary embodiments with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIGS. 4A-4B are a partial exploded perspective view of the guidance device and/or system of FIG. 3 and a close-up perspective view of a portion (indicated by dashed lines in FIG. 4A) of the at least one embodiment of the guidance device and/or system illustrated in FIG. 4A, respectively, in accordance with one or more aspects of the present disclosure;

FIG. 5B is a perspective view of at least a further embodiment of a guidance device and/or system for performing needle guidance having a hinge in accordance with one or more aspects of the present disclosure;

FIG. 6 is a schematic diagram showing an embodiment of a system for performing ablation and/or needle guidance planning and/or performance in accordance with one or more aspects of the present disclosure;

FIGS. 7A-7B are diagrams showing at least one embodiment of multi-probe medical procedure (e.g., ablation) in accordance with one or more aspects of the present disclosure;

FIG. 8 is a schematic diagram of at least one embodiment of a communication signal and/or electrical connection(s) between a first processor and a second processor of a guidance device and/or system in accordance with one or more aspects of the present disclosure;

FIGS. 9A-9B are diagrams showing at least two embodiments of communication sequence procedures for communication between a guidance device and/or system for performing needle guidance and at least an additional processor or computer in accordance with one or more aspects of the present disclosure;

DETAILED DESCRIPTION OF THE PRESENT INVENTION

One or more devices, systems, methods and storage mediums for performing guidance for needles or probes are disclosed herein. In one or more embodiments, the configurations, methods, apparatuses, systems and/or storage mediums may be combined to further enhance the effectiveness in guiding the needles or probes, including in guiding the needles or probes wirelessly. Several embodiments of the methods, which may be carried out by the one or more embodiments of an apparatus, system and computer-readable storage medium, of the present disclosure are described diagrammatically and visually in FIGS. 1 through 15.

Figure 1:
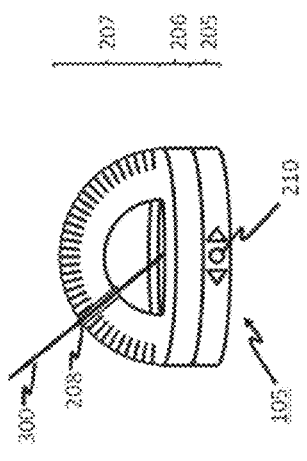
FIG. 1 is a schematic diagram showing an embodiment of a guidance device and/or system for performing needle guidance in accordance with one or more aspects of the present disclosure.
Figure 2:
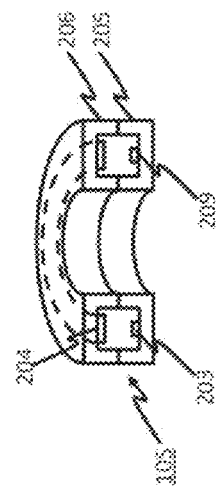
FIG. 2 is a schematic diagram showing a section view of the guidance device and/or system of FIG. 1 in accordance with one or more aspects of the present disclosure.

In accordance with at least one aspect of the present disclosure, at least one embodiment of a device for guiding needles or probes may include structure as shown in FIGS. 1-2. In FIG. 1 there is a guidance device 105, which preferably includes a fixed part 205 and a movable part 206. The guidance device 105 may include a processor (also referred to herein as a "second processor") 1201, 1201' (while reference number 1201' is used to indicate a "second" processor, the structure discussed herein and shown in the accompany figures for the processor or CPU 1201 may be used in one or more embodiments of the guidance device 105), a wireless circuit 1205, 1212 (also referred to herein as a "second wireless circuit"; while reference numbers 1205 and 1212 refer to a communication interface and a network interface, respectively, as discussed below, the structure for both elements 1205 and 1212 may be used for the wireless circuit in one or more embodiments of the guidance device 105), and an encoder sensor 203. The guidance device 105 may further include, or be used with, one or more fiducial markers 209, one or more light emitting diodes (LEDs) 210, and/or one or more batteries 211 in one or more embodiments. A plurality of fiducial markers 209 may be included (embedded) in the device 105 (e.g., in the fixed part 205, in the movable part 206, etc.) for device to image registration.

Preferably, in one or more embodiments, the movable part 206 includes an encoder scale 204. The encoder scale 204 may be fixed on the movable part 206. In one or more embodiments, the fixed part 205 and the movable part 206 are removably attached to each other such that the encoder sensor 203 faces or is disposed towards the encoder scale 204 in a case where the fixed part 205 and the moveable part 206 are attached as best seen in FIG. 2. Alternatively, in one or more embodiments, the encoder scale 204 may be fixed on the fixed part 205, and the encoder sensor 203 may be disposed on the movable part 206 to achieve positional sensing between the fixed part 205 and the moveable part 206.

Preferably, in one or more embodiments, the encoder sensor 203 operates to detect a relative position with respect to (and/or based on interaction with or sensing) the encoder scale 204. In embodiments where the encoder sensor 203 is fixed on the fixed part 205, relative displacement between the fixed part 205 and the movable part 206 may be detected by the encoder sensor 203 and/or an encoder.

Preferably, in one or more embodiments, the movable part 206 further includes an arc 207 as best seen in FIG. 1. A needle holder 208 is preferably attached on, or may be used with, the arc 207. Preferably, the needle holder 208 is movable along the arc 207, and the needle holder 208 operates to hold a needle by one or more methods, including, but not limited to, friction, pressure fitting, a clasp or grasping mechanism, etc. Preferably the arc 207 (or a guidance surface) includes a scale (e.g., a tool or reference scale for measuring an angle of the needle or other item being held by the holder 208) so that a user of the device or system 105 may read an angle at which the needle or other item being held by the holder 208 is oriented. In one or more embodiments, the arc 207 may be releasably connected to the movable part 206 such that the arc 207 may be released from the movable part 206 as needed. In one or more embodiments, the arc 207 may be integral with the movable part 206.

Preferably, in one or more embodiments of the device or system 105, fiducial markers 209 (see e.g., the fiducial marker 209 shown in FIG. 2) may be used for registration of the device or system 105. Because fiducial markers 209 are visible in CT images, a processor, such as a first processor 1201 of a computer 2, 2' (see e.g., FIG. 6 as discussed further below, First Processor 1201 as shown in FIGS. 8A-9 as discussed further below and FIGS. 14-15 as discussed further below, etc.) and/or the second processor 1201' of the guidance device or system 105, may calculate an orientation of the guidance device 105 based on the positions of a plurality of the fiducial markers 209. In one or more embodiments, fiducial markers 209 may be implanted in the fixed part 205 and placed uniquely in a three dimensional (3D) space.

An insertion angle of a needle 300 (e.g., one or more needles use for a medical procedure as discussed herein, such as, but not limited to, ablation, biopsy, etc.) is preferably guided by a combination of the scale on the arc 207, a position of the encoder sensor 203 and orientation of the guidance device or system 105 in one or more embodiments. If a user places the guidance device or system 105 on a designated or predetermined or predefined position, then the fiducial markers 209 may be optional or may not be used as needed. In such a step, a processor, such as the First Processor 1201, the Second Processor 1201', etc., does not need to calculate orientation in view of the preset orientation.

In one or more additional embodiments, the guidance device or system 105 may include additional or alternative features as shown in FIGS. 3-4B and 5, and as discussed in U.S. Provisional Patent Application No. 62/764,849, filed on Aug. 15, 2018, and U.S. patent application Ser. No. 16/539,769, filed Aug. 13, 2019, which applications are incorporated by reference herein in their entireties.

Figure 3:
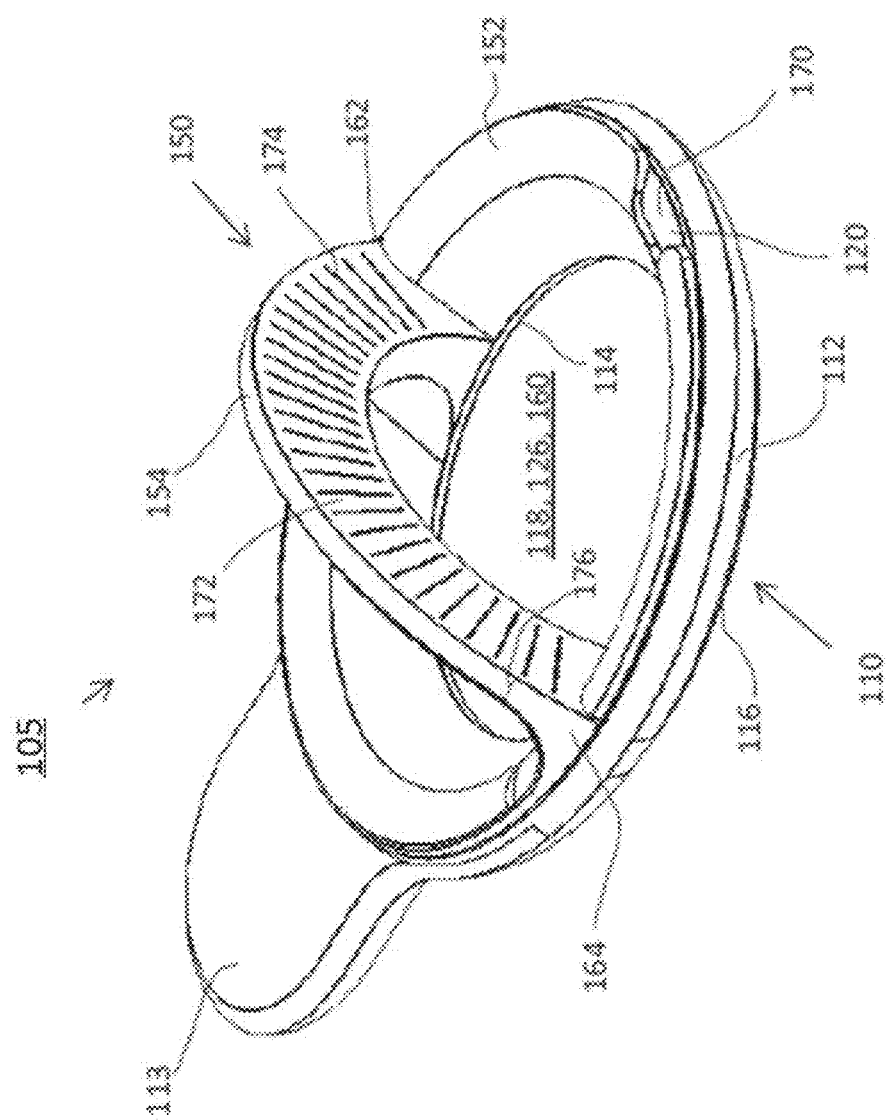
FIG. 3 is a schematic diagram showing at least one embodiment of a guidance device and/or system for performing needle guidance in accordance with one or more aspects of the present disclosure.

FIG. 3 illustrates the movable portion 150 (also referred to herein as the movable portion, such as the movable portion 206 in one or more embodiments) of the guide 105 coupled with the base assembly 110 (also referred to herein as the fixed portion, such as the fixed portion 205 in one or more embodiments). FIGS. 4A and 4B illustrate the moveable portion 150 of the guide 105 removed from the fixed portion, such as the base assembly 110. In one or more embodiments where the movable portion 150, 260 is referred to as the first portion or the first movable portion, then the fixed portion (e.g., the base assembly 110) may be referred to as the second portion. Similarly, in one or more embodiments where the movable portion 150, 260 is referred to as the second portion or the second movable portion, then the fixed portion (e.g., the base assembly 110) may be referred to as the first portion. In either scenario, there is a first portion and a second portion.

The base assembly 110 may include a base ring 112 in the form a ring shape having an inner circumference 114 and an outer circumference 116 (see FIG. 3). The inner circumference 114 defines an opening 118. The opening 118 provides access to the patient when the medical guidance device or system 105 is mounted onto a patient. That is, the opening 118 provides an area in which the patient's skin is exposed. The base ring 112 may also be referred to as a "fixed ring" or "stationary ring" because the base ring 112 is affixable to the patient and is not rotatable once affixed to the patient in one or more embodiments. The width of the base ring 112 (i.e., the distance from the inner circumference 114 to the outer circumference 116 in a radial direction, which is also the difference between the inner radius and the outer radius of the base ring 112), may be ⅙ to ½, more preferably ¼ to ⅓, the diameter of the opening 118. In one example, the outer diameter of the base ring 112 may be from 50 to 150 mm (for example 80 mm) and the inner diameter (i.e., the diameter of the opening 118) may be 30 mm to 110 mm (for example 60 mm).

The base assembly 110 may further include a moveable ring 120. The moveable ring 120 is best seen in FIG. 4A. The moveable ring 120 may be in the form of a ring shape having an inner circumference and an outer circumference. The inner circumference defines an opening 126 that provides access to the patient. The width of the moveable ring 120 (i.e., the distance from the inner circumference to the outer circumference in a radial direction of the ring 120, which is also the difference between the inner radius and the outer radius of the moveable ring 120), may be ⅙ to ½, more preferably ¼ to ⅓, the diameter of the opening 118, 126. In one or more embodiments, the opening 118 and the opening 126 may be the same size. In one example, the outer diameter of the moveable ring 120 may be from 50 to 150 mm (for example 75 mm) and the inner diameter (i.e., the diameter of the opening 126) may be 30 to 110 mm (for example 65 mm). The moveable ring 120 may also be referred herein as a "rotatable ring" because the moveable ring 120 is capable of rotating about an axis passing through a center point of the opening 118, 126. In one or more embodiments, the center point is the center of the circular opening 126 defined by the inner circumference 122. The axis may extend vertically through the center point, i.e., perpendicularly relative to a horizontal plane defining the surface to which the base assembly 110 may be mounted.

The moveable ring 120 may rotate relative to the base ring 112 via a bearing 128, as discussed in U.S. Provisional Patent Application No. 62/764,849, filed on Aug. 15, 2018, and U.S. patent application Ser. No. 16/539,769, filed Aug. 13, 2019, which applications are incorporated by reference herein in their entireties. In such an embodiment, the base ring 120 may be referred to as a fixed ring because it is not rotatable, while the moveable ring 120 may be referred to as rotatable ring because it is rotatable relative to the base ring 120 via the bearing 128. The bearing may be a ball bearing or any other suitable bearing structure known in the art that allows for relative motion between two concentric rings or similarly sized and/or shaped mating portions of the device or system 105. For example, the bearing may be a plain bearing, a roller bearing, and the like. The base assembly 110 may further include a seal 129. The seal 129 protects the bearing 128 by preventing contamination from the external environment from coming into contact with the bearing 128.

In one or more embodiments, the fixed portion 205 or the base assembly 110 may further include a grip 113 as best seen in FIGS. 3 and 4A. The grip 113 may be attached to or integral with the base ring 112. The grip provides a mechanism for the operator to increase stability of the base assembly 110 during insertion of the medical instrument. Additionally, the grip 113 may house electronic components relating to the use of LED arrays, which is discussed below with respect to FIG. 5A. The grip may also include visible markers for the medical images.

The upper or first movable portion 150 of the guide 105 may comprise a frame 152 and an arc member 154. The frame 152 may have a ring shape similar to the base ring 112 and the moveable ring 124. The frame 152 may have an inner circumference 156 and an outer circumference 158. The inner circumference 156 defines an opening 160. The opening 160 provides access to the patient. The width of the ring shape of the frame 152 (i.e., the distance from the inner circumference 156 to the outer circumference 158 in a radial direction, which is also the difference between the inner radius and the outer radius of the frame 152), may be ⅙ to ½, more preferably ¼ to ⅓, the diameter of the opening 118, 126, 160. In one example aspect, the outer diameter of the frame 152 may be from 50 to 150 mm (for example 75 mm) and the inner diameter (i.e., the diameter of the opening 160) may be 30 to 110 mm (for example 65 mm). In one or more embodiments, the openings 118, 126, 160 may be the same size or substantially the same as each other.

As shown in FIGS. 3 and 4A, the arc member 154 may include a first end 162 and a second end 164. Each of the ends 162, 164 may connect to the frame 152 on diametrically opposed sides of the frame 152, thereby bisecting the frame 152 in a first half or portion 166 and a second half or portion 168. In various embodiments, the arc member 154 may be hinged at a first end 162 for pivotal attachment to the frame 152, with a fastener at the second end 164, such that the arc member 154 may be pivoted. In other embodiments, the second end 164 may be affixed to the frame 152 by a locking device or other fastener intended to removably affix the arc member 154 to the frame 152. In yet additional embodiments, the arc member 154 may be removably attached to the frame 152 at both the first end 162 and the second end 164, thus allowing for complete removal of the arc member 154. The first end 162 and second end 164 may be affixed to the frame 152 by a locking device or other fastener (e.g., a pin, an R-clip, a spring-clip, etc.) intended to removably affix the arc member 154 to the frame 152. It is further contemplated that the arc member 154 may be slideably attached to the frame 152 at the first end 162 and/or second end 164 to facilitate removal and reattachment of the arc member 154.

The frame 152 may include a gap 170 (best seen in FIGS. 3 and 4A) such that the second half or portion 168 of the frame 152 is non-continuous. That is, the gap 170 serves as an interruption in the second half or portion 168 of the frame 152. The gap 170 may be sized such that a medical instrument may pass through the gap 170 into opening 160 of the frame 152. The medical instrument can be an ablation probe in cryoablation, microwave ablation, radiofrequency ablation, laser ablation and irreversible electroporation ablation. Also, the medical instrument can be a needle-like device, for example a biopsy needle, an aspiration needle and a drainage needle. The gap 170 includes the width wide enough to get the medical instrument through for releasing/accepting. In other words, the gap 170 may extend from the inner circumference 156 to the outer circumference 158 of the frame 152 to provide a pathway for an instrument to exit the frame 152, as will be discussed below. The gap 170 may extend radially relative to the center of the opening 160 through the frame 152. The gap 170 may also extend non-radially (i.e., angled relative to the center of the opening 160). The first half or portion 166 of the frame 152 may be continuous and lacking any gap. That is, from the point on the frame 152 where the first end 162 of the arc member 154 meets the frame 152 to the point on the frame 152 where the second end 164 of the arc member 154 meets the frame 152, the frame 152 is a continuous structure. In other words, the first half 166 of the frame 152 has a closed structure while the second half 168 of the frame 152 has a non-closed/open or interrupted structure.

The arc member 154 has an arc shape that spans an angle relative to the horizontal plane (see e.g., FIGS. 3 and 4A; see also, embodiment with the arc 207 spanning an angle). The angle 170 may be from 60 to 170 degrees, more preferably 120 to 150 degrees. The angle may be from 0 to 180 degrees in one or more embodiments. The arc member 154 may include a guide surface 172 that provides a guidance area for the instrument. The arc member 153 may include a plurality of angular reference marks 174 on the guide surface or guidance surface 172 one or more of the references marks 174 may be referred to as a scale or reference scale). The guide surface 172 may have a different color than the color of the surface on the opposite side of the arc member 154. Having a different color allows the operator to quickly and easily ascertain which surface is the guide surface. This is particularly useful in an embodiment which lacks the plurality of reference marks, as discussed below. The angular reference marks 174 signify an angle around center point of an opening, such as the opening 118, 126, or 160 as aforementioned.

The use of the angular reference marks 174 (or the markings shown in FIG. 1) is described below as part of a method of guiding a medical instrument. The angular reference marks may be visible optically as well as in CT and X-ray images utilizing radio-opaque material. The radio-opaque material may be, but is not limited to, plastic including fillers of barium sulfate, bismuth subcarbonate, bismuth oxychloride, tungsten, etc. The arc member 154 may have a thickness 176. The thickness 176 may be ¹⁄₁₅ to ⅓ the diameter of the opening 160, more preferably ¹⁄₁₂ to ⅕ the diameter of the opening 160, more preferably ¹⁄₁₀ to ⅕ the diameter of the opening 160. In various embodiments, the angular reference marks 174 may be provided on the thickness 176 portion of the arc member 154, thus allowing for viewing of the angle from a top perspective. The angular reference marks 174 may be envisaged in any desired increment and/or scale, with various increments being sized differently for indication purposes.

The ends 162, 164 of the arc member 154 may be integrally formed with the frame 152 such that the entire upper or first portion 150 of the device 105 and/or the device 105 is monolithically formed. That is, the entire upper or first portion 150 of the device and/or the device 105 may be cast as a single piece of material. Additionally, as shown in FIG. 4B, each of the ends 162, 164 may include a fillet structure 178 on the side of the arc member 153 that transitions to the closed first half 166.

In some embodiments, the plurality of angular reference marks 174 on the guide surface 172 may comprise LED indicators. These LED indicators provide illumination of the guide surface or they may be turned on to indicate, for example, an angle of planned entry (e.g., a lit indicator appears at the planned entry angle). For a medical guidance apparatus that is configured to detect the angle of a needle positioned in or near the medical guidance apparatus, the LEDs may be used to display when the needle is approaching or at a 'correct angle' by, for example, signaling with a green light at that angle.

Each of the monolithic structure of the first or upper portion 150, the device 105, the closed structure of the first half or portion 166 of the frame 152, the thickness 176 of the arc member 154, and the fillet structure 178 contributes to one or more structural advantages. For example, when force is applied to the arc member 154 in a direction against the guide surface 172, one or more of these structural features provide sufficient stiffness and rigidity to provide support and to minimize deflection, thereby providing sufficient support to the user when position an instrument. This structure provides a high rigidity while the structure still provides an opening for needle egress. This is in contrast to a cantilever shape, i.e., an open frame. The monolithic structure has a greater stiffness and may withstand the forces associated with needle placement and maneuvering with smaller deflection. Further, the stiffness of the closed first half or portion 166 may be increased by increasing thickness of the closed first half or portion 166 while keeping the gap 170 in the second half or portion 168.

Additionally, because of the monolithic structure(s), assembly error may be avoided in one or more embodiments. The structure of the guide 105 and/or the upper or first portion 150 is able to provide this structural support despite having the gap 170 in the second half 168.

As best seen in FIG. 4A, the base assembly 110 and the upper or first portion 150 of the guidance device 105 may each include corresponding taper portions 130, 180, respectively. The taper portion 130 of the base assembly 110 may be formed as part of the moveable ring 120 and may extend around the entire circumference of the moveable ring 120. The taper portion 180 of the upper or first portion 150 of the guidance device 105 may be formed along the entire circumference of the frame 152. The two taper portions 130, 180 may be congruently formed such that taper 180 of the guide 150 geometrically fit within the taper portion 180 of the base assembly 110. By having a congruent geometry, the upper or first portion 150 of the guidance device 105 may easily mate with the base assembly 110 via the taper portions 130, 180. In addition to allowing for easier mating, the taper provides greater range of angles for the reference marks 174 than as compared to a non-tapered configuration. Furthermore, the taper feature increases the structural rigidity of the arc member 154 against the force of the medical instrument imparted on the arc member 154 during guidance. In another aspect, when no moveable ring is present (discussed below), the taper portion of the base assembly may instead be formed in the base ring 112. In such an arrangement, the taper portion 180 is geometrically congruent with a taper portion of the base ring 112 in the same manner that the taper portion 180 may be geometrically congruent with the taper portion 130 of the moveable ring 120. In other words, the taper portions may be used to directly frictionally mate the upper or first portion 150 of the guidance device 105 with the base ring 112. However, the specific angle(s) of the taper is not limiting based on the discussion herein. In some embodiments, the taper portions 130, 180 of the base assembly 110 and the upper or first portion 150 of the guidance device 105 may be understood as a conical interface, where the base assembly 110 and the upper or first portion 150 of the guidance device 105 are geometrically aligned at the taper portions 130, 180 to the center axis of the conical interface. Kinematically, this interface eliminates in-plane relative motion between the base assembly 110 and guide 150 while allowing the guide 130 to rotate.

As noted above the upper or first portion 150 of the guidance device 105 may be rotatably coupled with the base assembly 110. In one aspect, this may be achieved by mechanically coupling the frame 152 of the upper or first portion 150 of the guidance device 105 to the moveable ring 120 via a mechanical interface as discussed in U.S. Provisional Patent Application No. 62/764,849, filed on Aug. 15, 2018, and U.S. patent application Ser. No. 16/539,769, filed Aug. 13, 2019, which applications are incorporated by reference herein in their entireties. The mechanical components may be any suitable mating structure such as corresponding male/female components, snap fitting, bayonet mount and Velcro-style fastener, and the like. One specific example of the mechanical interface is shown in FIGS. 4A and 4B. FIG. 4A shows the first mechanical component 182*b* and FIG. 4B shows the second mechanical component 182*a*. In this example, the first mechanical component 182*b* is a key, while the second mechanical component 182*a* is a keyway. While only one keyway is shown in FIG. 4B, a second keyway on the symmetrically opposite end of the arc member 154 may also be present to mate with the opposing key shown in FIG. 4A. The first mechanical component 182*b* (e.g., keys) may be configured to be aligned to a plane position of the guide surface 172. Also, as seen in FIG. 4B, the second mechanical component 182*a* (e.g., keyways) may include part of the guide surface 172. Accordingly, when mating the first mechanical component 182*b* (e.g., keys) with the second mechanical component 182*a* (e.g., keyways), the arc member 154 will have a predetermined orientation/alignment relative to the base assembly 110.

Once the upper or first portion 150 of the guidance device 105 is mated with base assembly 110 via the moveable ring 120, the upper or first portion 150 of the guidance device 105 is able to freely rotate via the moveable ring 120. That is, the moveable ring 120 being rotatable about an axis relative to the stationary base ring 112 (as described above), and the upper or first portion 150 of the guidance device 105 being coupled with the moveable ring 120, allows the upper or first portion 150 of the guidance device 105 and the moveable ring 120 to rotate together about the axis when a rotational force is applied to either the moveable ring 120 or the upper or first portion 150 of the guidance device 105.

Figure 5A:
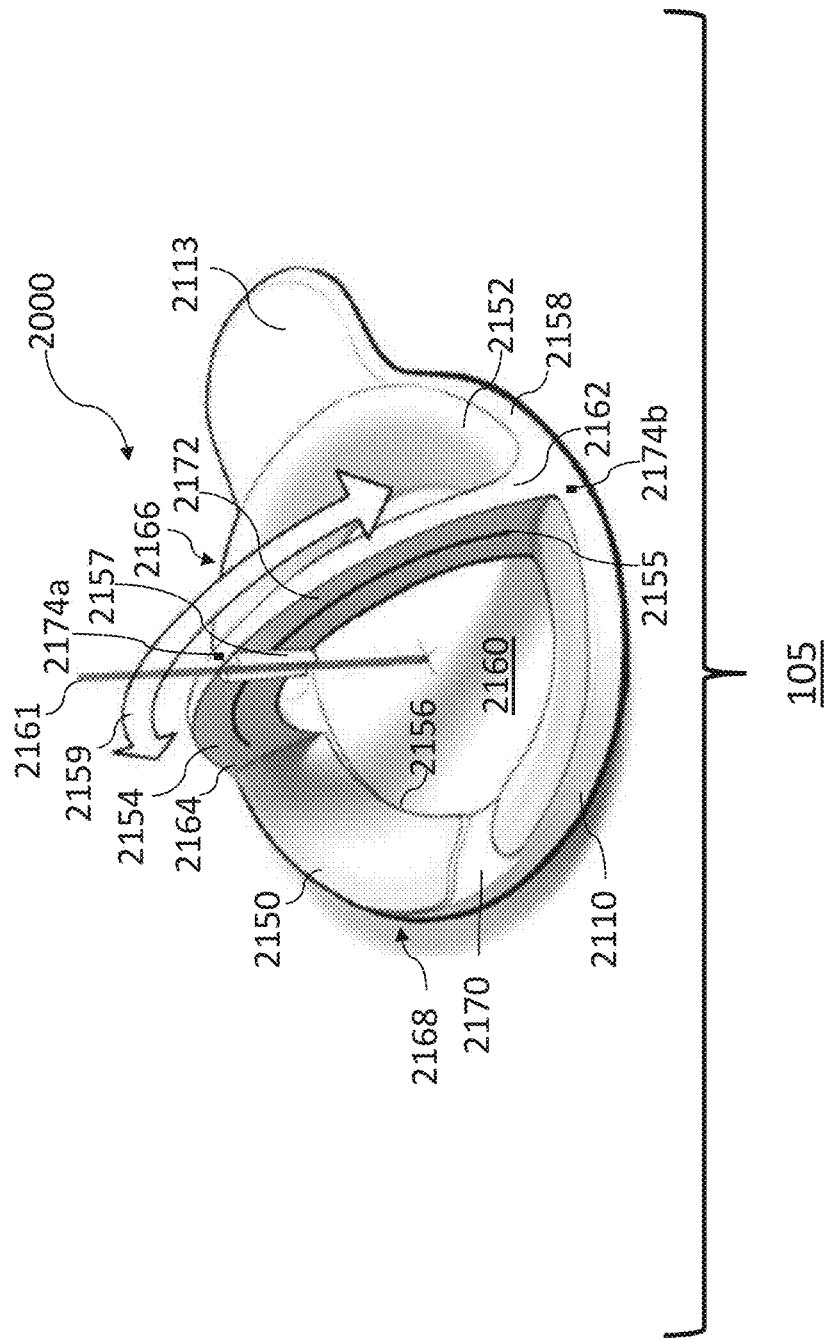
FIG. 5A is a perspective view of at least another embodiment of a guidance device and/or system for performing needle guidance in accordance with one or more aspects of the present disclosure.

A further embodiment of a needle guidance device or system is shown in FIG. 5A. FIG. 5A illustrates a perspective view another embodiment of a medical guidance apparatus 2000 having a guide or upper movable portion 2150 and a base assembly 2110. The base assembly 2110 and the guide or upper movable portion 2150 are similar to the base assembly 110 and the upper movable portion 150 of the device 105 as discussed above, especially in reference to FIGS. 3-4B, and similar reference numbers represent corresponding features. Thus, the base assembly 2110 may similarly include a stationary base ring and a moveable ring. The guide or upper movable portion 2150 similarly may include a frame 2152, an arc member 2154, an inner circumference 1156, an outer circumference 2158, an opening 2160, a first end 2162 and a second end 2164, a first half 2166, a second half 2168, a gap 2170, a guide surface 2172, and an arc member thickness.

The width of the ring shape of the frame 2152 (i.e., the distance from the inner circumference 2156 to the outer circumference 2158 in a radial direction, which is also the difference between the inner radius and the outer radius of the frame 2152), may be the same as in frame 152. The arc member 2154 may have an arc shape that spans the same angle range as in the arc member 154. The arc member 2154 may be integrally formed with the frame 2152 such that the entire guide or upper movable portion 2150 is monolithically formed, as with the guide or upper movable portion 150. Thus, the guide or upper movable portion 2150 has the same structural advantage as noted above with the guide or upper movable portion 150.

Similar to the guide or upper movable portion 150, the guide or upper movable portion 2150 may be rotatably coupled with the base assembly 2110. The guide or upper movable portion 2150 may be coupled via the same mechanical components noted above or with another mechanism. A corresponding feature may be present on the moveable ring or base ring to couple the guide or upper movable portion 2150 to the base assembly 2110. The guide or upper movable portion 2150 may rotate in the same manner as the guide or upper movable portion 150.

A difference between the guide or upper movable portion 2150 and the guide or upper movable portion 150 is provided in the arc member 2154. As shown in FIG. 5A, the arc member 2154 may comprise a rail 2155 and an instrument holder 2157. The rail 2155 may be formed in the guide surface 2172 and may have an arc shape along the same arc path defined by the arc member 2154. The instrument holder 2157 may be slideable along the rail 2155 along the path shown by the arrow 2159. The instrument holder 2157 may be in the shape of a half cylindrical groove sized to receive an instrument 2161, for example a needle. The instrument holder 2157 may be shaped to fit other instruments, depending on the procedure being conducted. The instrument holder 2157 provides constrained guidance for the instrument 2161. The instrument holder 2157 can accurately guide the instrument 2161 by directing the half cylindrical groove to the target trajectory. Thus, the instrument holder 2157 can increase accuracy and can reduce intervention.

The instrument holder 2157 may be shaped to fit multiple instruments in a pre-set geometric configuration, for example multiple cryo-ablation needles arranged so the two or more needles will be held by the instrument holder 2157. For example, two needles may be held simultaneously, both positioned near the arc member 2154 or tangential to the arc member 2154. In other examples, three, four, or more needles may be held simultaneously by the instrument holder 2157 in a triangle, square, diamond, etc. configuration. The instrument holder 2157 may provide constrained guidance for the instruments to maintain the geometric relationship between instruments (e.g., parallel insertion) during the procedure.

Another difference shown in FIG. 5A is the use of illumination indicator 2174a in place of physical marks used in the other embodiment examples. That is, as seen in FIG. 5A, there are no line marks as in the above-described embodiments. Rather, as shown in FIG. 5A, the illumination indicator 2174a may be placed along the topside of the arc member 2154. The illumination indicator 2174a may serve the same function of the marker discussed above. While one illumination indicator 2174a is shown on the arc member 2154 (because only one is lit up), there may be a plurality of illumination indicators along the entire span of the arc member at the same intervals of the hatch marks shown in the other embodiments. Only one illumination indicator may be lit up, in one or more embodiments, during use to show the operator where the instrument should be placed along the arc member. Thus, the illumination indicator 2174a in FIG. 5A is showing the current desired position of the instrument. With the illumination indictor 2174a, rather than the operator needing to visually find a particular marker along the arc, the operator can easily and quickly see where to place the instrument along the arc. Another illumination indicator 2174b may be provided on the outer circumference of the base ring. The illumination indicator 2174b may serve the same function as the other illumination indicator with regard to the desired rotational position of the guide or upper movable portion 2150. The illumination indicator 2174b may indicate the insertion plane. Accordingly, the illumination indicators with respect to the base ring may also be present along the entire circumference, while only a single indicator is illuminated in the example shown in FIG. 5A. Thus, because the operator does need to read the angular reference marks, the duration of the intervention as well as mental stress of the operator is reduced. The illumination indicators may be an LED array for which the electronics to electrically drive the array are stored in a grip 2113. It should be understood that the illumination indicators may be applied to any of the other example embodiments disclosed herein. That is, the use of the illumination indicators is not a mutually exclusive feature and may be used in place of or alongside the hatch marks and/or may be used with auditory or audio-based indicators (or, in one or more embodiments, the auditory or audio-based indicators may be used alone or with one or more of the illumination or visual indicators and/or hatch marks). The guide surface 1172 and/or the entire second half or portion 2168 of the frame 2152 may be a different color than the side of the arc member opposite the guide surface and/or the first half or portion 2166 of the frame 2152.

Another optional feature of some embodiments that is illustrated in FIG. 5A is a differentiating marker located on the guide or upper movable portion 2150. The differentiating marker is shown as a different color or hue (see e.g., shaded areas around elements 2172, 2157, 2150, 2152, etc. of the device 105 in FIG. 5A) located on the surfaces of the guide or upper movable portion 2150 visible during use. This differentiates the portion of the medical guidance apparatus, device or system where the needle will be placed and guided. The differentiating marker may be, for example, a different color, an adhesive, a pattern, or some other differentiator that the physician or clinician can use to quickly differentiate which portion of the device should be used during needle placement.

Yet a further embodiment of a needle guidance device or system using a hinge is, for example, shown in FIG. 5B. One or more hinged arc embodiments may be used with one or more features of the instant application, including any of the hinged guidance apparatuses discussed in at least U.S. Provisional Patent App. No. 62/764,820, filed Aug. 15, 2018, in at least U.S. Provisional Patent App. No. 62/875, 243, filed Jul. 17, 2019, in at least U.S. Provisional Patent App. No. 62/764,849, filed Aug. 15, 2018, and in at least U.S. patent application Ser. No. 16/539,769, filed Aug. 13, 2019, each of which applications are incorporated by reference herein in their entireties. FIG. 5B illustrates a perspective view another embodiment of a medical guidance device or apparatus 105 having a guide or upper movable portion 206, a fixed portion 205, and an arc 207 using a hinge assembly 62, 64 (e.g., the arc 207 may be terminated at one end thereof with a hinge, such as, but not limited to, a c-shaped clip 62 to be disposed on, around or over a pin 64) where the hinge assembly 62, 64 is in an opened position or state. The fixed portion 205 and the moveable portion 206 are similar to the aforementioned base assembly 2110 and the guide or upper movable portion 2150, or the other base assembly 110 and the upper movable portion 150 of the device 105 as discussed above, especially in reference to FIGS. 3-4B, and similar reference numbers represent corresponding features. In this configuration the other end of the arc 207 has been un-clipped from the rotating ring of the moveable portion 206 and the entire arc 207, including the probe holder 70 (which is similar to other probe or needle holders, such as element 2157 shown in FIG. 5A), is removed out of an insertion path 55. In the open position, the arc 207 may be positioned in one or more orientations, for example, substantially perpendicular to a plane of the ring of the moveable portion 206 or the fixed portion 205. However, if more space is needed for access to the area of interest, the first end of the arc 207 may also be detached at the pivotable hinge assembly 62, 64. To that end, the pivotable hinge assembly 62, 64 may be designed in other ways known to those skilled in the art such that the hinge assembly 62, 64 operates to pivot as a hinge, and is not limited to the c-shaped clip 62 and pin 64 configuration. This design allows the guide device (guidance system) 105 to be used in a variety of interventional and/or medical procedures.

For example, during a needle insertion procedure, it is highly advantageous that the arc 207 is rigidly attached at both ends thereof to the ring moveable portion 206 (e.g., as shown in at least FIG. 1). However, either before or after needle insertion procedure, the arc 207 may be entirely separated (removed) from the ring of the moveable portion 206. As mentioned above, the fixed portion 205 is configured to be strapped onto the patient's body to avoid accidental movement. Therefore, at the beginning of a procedure, only the fixed portion 205 and the ring of the moveable portion 206 may be attached to the patient's body to give the physician the opportunity to arrange the guide device 105 on the precise location of needle insertion.

On the other hand, after a needle insertion procedure is completed, e.g., after a first needle has been inserted, the physician may need to access the insertion point for inspection or confirmation. In that case, the arc 207 may be unlocked from the ring of the moveable portion 206 by operating the snap joint locking mechanism 80, and then the arc 207 is pivotably rotated to the position shown in FIG. 5B. This gives access to the physician for the necessary observation and confirmation of needle insertion. In addition, if more room is necessary for access to the insertion area of interest, the arc 207 may be disengaged from the pin 64 (e.g., the c-shaped clip 62 may be disengaged from the pin 64) of the ring of the moveable portion 206 so that the entire arc 207 and the needle holder 70 may be removed from the ring of the moveable portion 206 and/or the moveable portion 206. However, even after the arc 207 and needle holder 70 are removed, the fixed portion 205 and the ring of the moveable portion 206 and/or the moveable portion 206 may still remain rigidly attached to the patient's body. To that end, a latch cam 40 may be provided at any position along the circumference of the ring of the moveable portion 206 to maintain the ring of the moveable portion 206 and/or the moveable portion 206 in a fixed (anti-rotating) position.

Therefore, in the event that a new needle-insertion procedure is being performed on the patient, e.g., in the case of having to use multiple needle-like instruments, the arc 207 including the needle holder 70 may be simply mounted back onto the ring of the moveable portion 206 and/or to the moveable portion 206 by engaging the pivotable hinge assembly 62, 64 (e.g., by reconnected the hinge clasp 62 to the pin 64) and click-mounting the arc locking mechanism 80. In this manner, this pivotable and removable arc 207 and the needle holder 70 may provide at least: (i) ease of access to the area of interest, (ii) stiff and rigid support for needle-like instrument insertion, (iii) precise guidance during instrument insertion, and (iv) effective repeatability of insertion because the fixed portion 205 and the ring of the moveable portion 206 and/or the moveable portion may remain rigidly attached to the patient's body at all times during a medical procedure.

In accordance with at least one aspect of the present disclosure and as aforementioned, one or more methods for performing needle guidance planning and/or performance and one or more methods for wirelessly guiding needles are provided herein. At least FIGS. 8A-8B and 10-13 illustrate communication sequences and/or flow charts of at least one respective embodiment of a method for performing needle guidance and/or performance using a guidance device (e.g., such as a device 105 as shown in FIG. 6), system (e.g., such as a system 10 as shown in FIG. 6) or storage medium. At least one embodiment of a system 10 may include a medical device (e.g., an ablation device, a biopsy device, etc.) 1, a needle guidance planning and/or performance computing system (which may include software and/or hardware for implementing the needle guidance planning and/or performance) or computer/processor 2 (alternative embodiment of a computer 2' that may be used is discussed herein below), a needle guidance device (such as, but not limited to, an image-plane localizer) 105, a Picture Archiving and communication system (PACS) 4 and an image scanner 5 (such as, but not limited to, a CT scanner, MRI device or other scanning apparatus). As shown diagrammatically in FIG. 6, the needle guidance planning and/or performance methods of the present disclosure may be involved with all major aspects of needle guidance planning and performance, including wirelessly guiding one or more needles or other medical devices. For example, the system 2 may communicate with the image scanner 5 to request information for use in the needle guidance planning and/or performance, such as, but not limited to, bed or slice positions, and the image scanner 5 may send the requested information along with the images to the system 2 once a clinician uses the image scanner 5 to obtain the information via scans of the patient. By way of another example, the system 2 may communicate and be used with a guidance device (also referred to as a locator device) 105 (such as an image-plane localizer that may be a patient-mount device and may be rotated as shown to help locate to biological object, such as a lesion or tumor; the aforementioned embodiments shown in FIGS. 3-5 may also be employed in the system 2 as the guidance device) to obtain information from the patient when conducting needle guidance planning and/or performance. The system 2 may further communicate with a PACS 4 to send and receive images of a patient to facilitate and aid in the needle guidance planning and/or performance. Once the plan is formed, a clinician may use the system 2 along with a medical device (e.g., an ablation device, a biopsy device, etc.) 1 to consult a chart or plan (e.g., for needle guidance, for ablation, for biopsy, for a medical procedure, etc.) to understand the shape and/or size of the targeted biological object to undergo the medical procedure (e.g., ablation, biopsy, etc.). Each of the medical device 1, the system 2, the guidance device 105, the PACS 4 and the scanning device 5 may communicate in any way known to those skilled in the art, including, but not limited to, directly (via a communication network) or indirectly (via one or more of the other devices 1, 105 or 5; via one or more of the PACS 4 and the system 2; via clinician interaction; etc.). In one or more embodiments as discussed herein, the guidance device 105 may communicate wirelessly with one or more of the following: the medical device 1, the system 2, the PACS 4, and the scanning device 5. Preferably, in one or more embodiments, the guidance device 105 communicates wirelessly with at least the system 2 or any other processor operating to interact with the guidance device 105 to perform the needle guidance planning and/or performance.

One or more embodiments of the needle guidance planning and performance apparatuses and systems, and methods and storage mediums may operate to improve the determination of the needle or probe (and/or other medical device) trajectory. One or more embodiments of the present disclosure operate to reduce the number of scans, and consequently reduce the insertion and trajectory determination time. One or more embodiments greatly assist clinicians, including during the stages of determining insertion point, determining trajectory, performing initial probe insertion and performing full probe insertion, by providing a probe tracking and guidance system for faster execution of the medical procedure and needle guidance plan and better accuracy in positioning a probe or other medical device. The tracking and guidance system not only tracks the probe, needle, guidance device, and/or other medical device position and orientation, but also provides cues for visualization software with the target biological object (e.g., a patient's lesion, a patient's tumor, etc.) and critical structures from an IR's or other clinician's point of view. This visualization may be updated in real time to account for motion due to respiration and tissue deformation. The tracking and guidance system can also give IR the ability to define the trajectory and insert the probe remotely through a robotic device placed on the body of the patient or situated near the patient, controlling the probe from outside of the imaging (CT for example) suite. The remotely controlled operating system may shorten procedures by reducing the time moving in and out of the CT suite and mitigating the exposure to radiation.

In one or more embodiments, multi-probe or multi-needle guidance (e.g., as shown in FIGS. 7A-7B) may be used in combination with any feature disclosed herein, including, but not limited to, guidance of the one or more needles or one or more probes (including wireless guidance thereof), with a margin map, with a medial axis or center line, with a security or credential check, etc. In one or more embodiments, the size and shape of a biological object, such as a lesion or tumor, may be used to determine whether two or more needles, and two or more probes/balloons, are needed to appropriately perform a medical procedure on the target area of the biological object (e.g., ablate a target ablation zone). In one or more embodiments, clinicians may employ a spherical balloon(s) for an ablation zone because it is easy to control. In one or more embodiments, the balloon or balloons may have a different shape, e.g., elliptical or other predetermined shape. Additionally or alternatively, the type of balloon and number of balloons/needles may vary depending on the type of ablation being performed. For example, when performing microwave ablation, RF ablation, laser ablation and/or cryoablation, a spherical balloon may be used or the ablation may require a shape other than spherical. As shown in FIGS. 7A-7B, multi-probe or multi-needle procedures are useful. For example, ablation may be performed with two needles and multiple balloons 140a, 140b to ablate a target ablation zone for a biological object, such as a tumor or lesion. As also shown in FIGS. 7A-7B, the methods disclosed herein may be used to simulate or perform needle guidance planning when evaluating a biological object or a target/target zone and determining whether to use a two-needle (or more) insertion for a desired medical procedure (e.g., ablation, biopsy, etc.).

Preferably the image scanner 5 (best seen in FIGS. 6 and 8) (e.g., a CT scanner) operates to generate one or more images from scanning a patient body (or portion thereof) with and/or without the use of the guidance device 105.

At least a first processor (e.g., a processor or CPU 1201 of the system 2 shown in FIG. 6, the first processor 1201 of FIG. 8, a processor or CPU 1201 in a device as shown in system 2 of FIG. 14, a processor or CPU 1201 as shown in system 2 of FIG. 15, a processor or CPU 1201 in another device, etc.) operates to load scanned images (e.g., from the PACS 4 generally as aforementioned because scanned images may be stored in the PACS 4). In one or more embodiments, the first processor 1201 operates to load images from the image scanner 5 and/or from the PACS 4. The first processor 1201 preferably supports users (e.g., physicians, clinicians, etc.) to plan and/or perform needle or medical device guidance trajectories (which may include or involve one or more of insertion angle(s), depth(s), region(s) of target(s) or interest(s), ablation power and duration if users use ablation needles, etc.). In one or more embodiments, the first processor 1201 may register scanned images and the guidance device 105 to calculate parameter(s) of one or more trajectories. In one or more embodiments, the first processor may read position information from an encoder (e.g., the encoder sensor 203) through a wireless connection.

The first processor 1201 may detect fiducial markers (e.g., the aforementioned fiducial markers 209) from images (e.g., CT images) automatically or may detect fiducial markers via manual user interaction. As aforementioned, detection of fiducial markers may not be needed when the guidance device 105 is placed on a designated or predefined position. In one or more embodiments, the first processor 1201 may operate to reconstruct oblique image(s) (although this is an optional feature that may not be used, for example, in a case where the system (e.g., the system 2) does not show reconstructed oblique images on a display (e.g., the display 1209 of FIG. 8, the display of FIG. 6, the display 1209 of FIG. 14, etc.). The first processor 1201 may allow users to compare pre-procedure images and post-procedure images (e.g., images taken before and after ablation).

Figure 14:
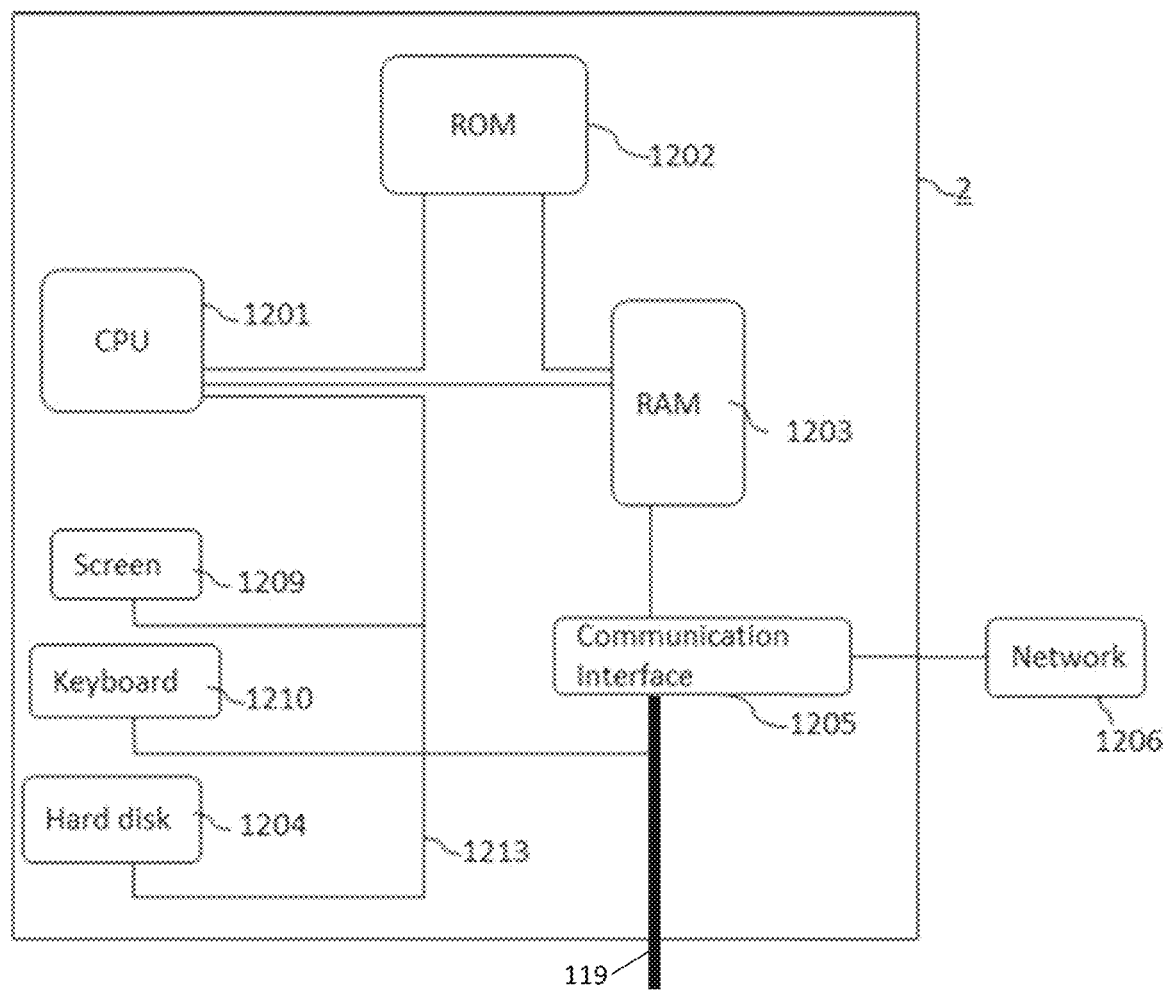
FIG. 14 shows a schematic diagram of an embodiment of a computer or processor that may be used with one or more embodiments of a needle guidance and/or performance method, apparatus or system in accordance with one or more aspects of the present disclosure.
Figure 15:
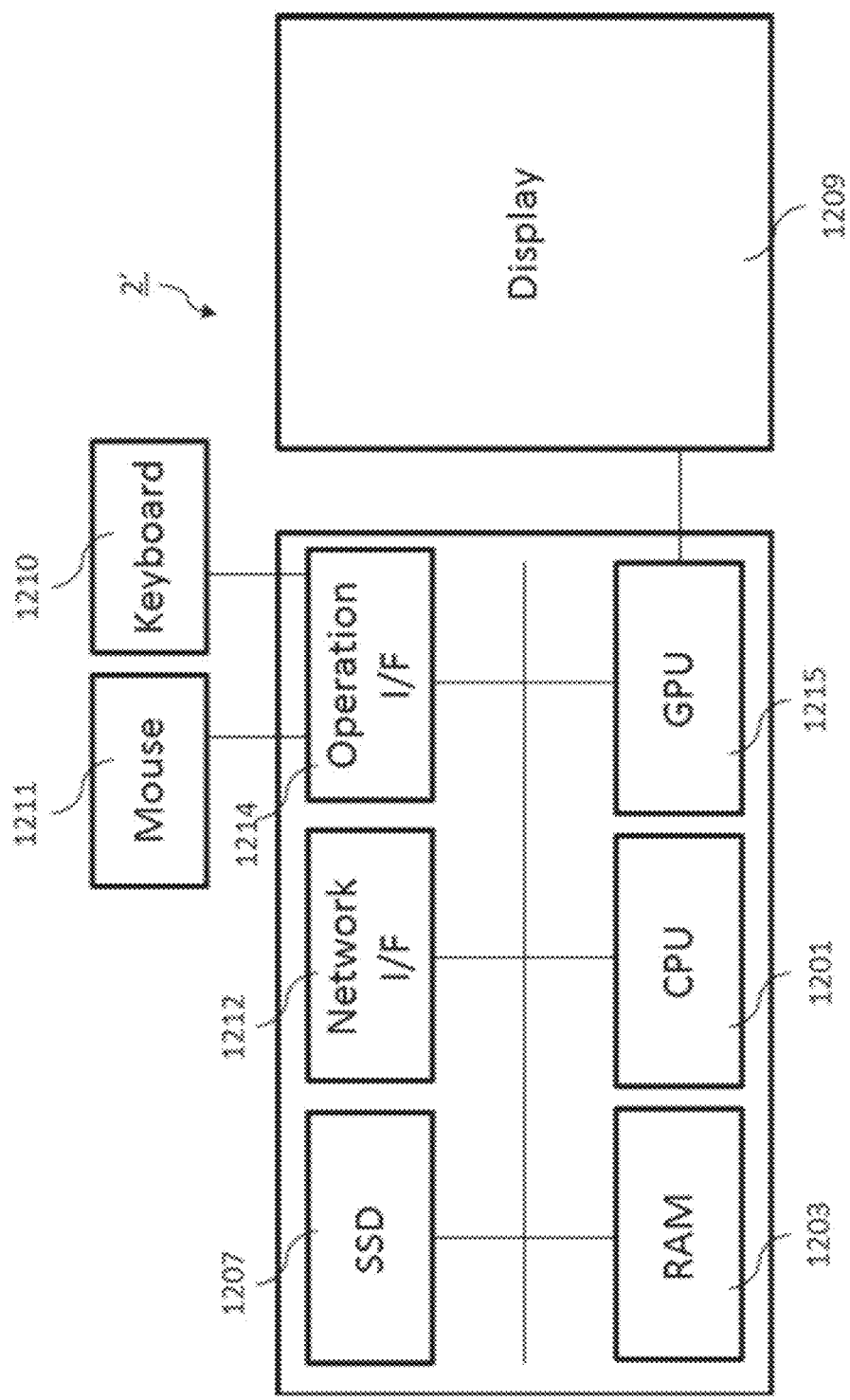
FIG. 15 shows a schematic diagram of another embodiment of a processor or computer that may be used with one or more embodiments of a needle guidance and/or performance method, apparatus or system in accordance with one or more aspects of the present disclosure.

A display (e.g., the display 1209 of FIG. 8, the display of FIG. 6, the display 1209 of FIG. 14, etc.) is preferably used in one or more embodiments to enable user interaction with an input device (e.g., a keyboard 1210 and/or a mouse 1211 as best seen in FIGS. 8 and 14-15). The display (e.g., the display 1209) may operate to do at least one or more of the following: show scanned images (e.g., CT images), show status (e.g., of the patient, procedure, one or more needles, etc.), visualize trajectories, compare pre-procedure and post-procedure images, etc.

Preferably, the first processor 1201 is connected to, and/or communicates with, a first wireless circuit (e.g., first wireless circuit 1205, 1212 as shown in FIG. 8, communication interface 1205 as shown in FIG. 14, network interface as shown in FIG. 15 (which may operate as a wired and/or wireless communication circuit), etc.) to enable communication between the first processor 1201 and at least a second processor (e.g., the second processor 1201' of the guidance device 105 as shown in FIG. 8, a processor of the system 2 or the system 2' as best seen in FIGS. 6 and 14-15, etc.).

Preferably, the second processor (also referred to herein as "the Second Processor") 1201' is connected to, and/or communicates with, a second wireless circuit (e.g., second wireless circuit 1205, 1212 as shown in FIG. 8, communication interface 1205 as shown in FIG. 14, network interface as shown in FIG. 15 (which may operate as a wired and/or wireless communication circuit), etc.) to enable communication between the first processor 1201 and the second processor 1201' to transfer information therebetween. In one or more embodiments, the second processor 1201' operates to do one or more of the following: read one or more positions from an encoder (e.g., the encoder sensor 203, the encoder sensor 203 based on interaction with the encoder scale 204, etc.); detect one or more errors of an encoder (e.g., the encoder sensor 203, the encoder sensor 203 based on interaction with the encoder scale 204, etc.) and/or the second processor 1201'; and control LEDs (see aforementioned discussion regarding LEDs, including, but not limited to, the discussion regarding elements 2174a, 2174b as shown in FIG. 5A, the LEDs 210 of FIG. 1, etc.).

In one or more embodiments, the guidance device 105 includes at least three LEDs to convey information to a user of the device 105. A center or middle LED may operate to indicate status information of the device 105 and/or the guidance status, and two other LEDs may indicate rotational direction for guidance. Various combinations of indicational patterns may be used for the LEDs. For example, in at least one embodiment, in a case where the center or middle LED is flashing, then the LED is indicating that an error occurred.

In a case where the center or middle LED is "On", then one or more guidance features are enabled. In a case where the center or middle LED is "Off", then the one or more guidance features are disabled. In one or more embodiments, when one of the other two rotational direction LEDs is flashing, then that indicates guidance is occurring and that the user should change the insertion angle in one direction. In one or more embodiments, when a second of the other two rotational direction LEDs is flashing, then that indicates guidance is occurring and that the user should change the insertion angle in a second direction. When both of the two rotational direction LEDs are on, then the one or more guidance features are enabled, and the user should stop adjusting the insertion angle. When both of the two rotational direction LEDs are off, then the one or more guidance features are disabled. In one or more embodiments, a frequency of the flashing of one or more of the LEDs may be used, and may change depending on distance (angle) between a current position and a target position. For example, in at least one embodiment, when a distance (angle) is long, the frequency may be low, and when the distance (angle) is near/short, then the frequency may be high. Other modifications to the number of LEDs, frequency of the flashing, information conveyed via the LEDs and configuration of the LEDs may be made depending on the information that a user desires to receive from the device 105 (and construction of the device 105 may occur based on such specifications).

In one or more embodiments, the information transferred between the first processor 1201 and the second processor 1201' includes one or more of the following: a position detected from an encoder (e.g., the encoder sensor 203 as aforementioned; in one or more embodiments, the detected position may be an angle position), a status of an encoder (e.g., the encoder sensor 203), a status of the second processor 1201', a status of the first processor 1201, a target position based on a trajectory or trajectories, a status of the guidance device 105, and a signal to enable or disable one or more guidance features of the guidance device 105. In one or more embodiments, an enable signal for the guidance device 105 may not be needed in a case where reception of target position information enables the one guidance features, and, in one or more embodiments, a disable signal for the guidance device 105 may not be needed in a case where the second processor 1201' stops the one or more guidance features automatically. In one or more embodiments, the signal to enable or disable one or more guidance features may include a guidance completion signal or information to be transferred between the first processor 1201 and the second processor 1201'.

Additionally, information conveyed by one or more components, such as, but not limited to, one or more of the device 105, the computer 2, the system 10, the first and second processors 1201, 1201', etc., may depend on the desired specifications for the guidance device and/or system. For example, structural attributes (defining how such components are structurally built to achieve the desired functional behavior) may change depending on a desired medical procedure. For example, in one or more embodiments, the guidance device 105, the system 10 and/or one or more other components of the system 10 may be used for the medical procedure of ablating tumors in a patient body. Because tumors may be invisible, users may confirm where tumors are using the image scanner 5 (e.g., a CT scanner) or other scan devices. The computer 2, the guidance device 105, and/or the guidance system 10 calculates an insertion point, an insertion angle, a depth, an ablation time and an ablation power of candidate trajectories, and users of the system 10 may input such calculated results into the system 10 for needle guidance planning and/or performance. After a trajectory users choose is set to the guidance device 105, users may insert the needle 300 (best seen in FIG. 1; e.g., the needle may be for ablation in an ablation procedure, a biopsy procedure, etc.) with the guidance device 105 accurately.

In one or more embodiments, users may turn on the whole guidance system 10 including the guidance device 105 at first. The guidance system 10 may establish a wireless connection between the first wireless circuit 1205, 1212 and the second wireless circuit 1205, 1212 in a startup routine.

After the preparation or the startup routine, a patient may be scanned by the image scanner 5 (e.g., the CT scanner 5 as shown in FIG. 8) with, or using, a disposable grid in one or more embodiments. The disposable grid operates to allow users find an insertion point more easily and more accurately. A disposable grid known to those skilled in the art may be used (such as, but not limited to, a Beekley Medical® Guidelines® CT Biopsy Grid 217, which may be obtained via Beekley Medical's website: https://www.beekley.com/Product-Details/GuideLines/CT-Biopsy-Grid-217). In one or more embodiments, users may use disposable fiducial markers (such as the aforementioned fiducial markers 209) instead of a disposable grid. Additionally or alternatively, users may find the insertion point without the grid and/or fiducial markers 209.

As aforementioned, in one or more embodiments, the first processor 1201 may load the scanned images, and may show the scanned images on the display 1209. A user or users of the system 10 may find a target region or regions from the scanned images and may set the target region or regions to the guidance system 10. The user or users may input data via one or more input devices (e.g., the keyboard 1210, the mouse 1211, etc.). Once settings and/or data are input, the first processor 1201 may then commence interaction for the needle guidance planning and/or performance.

After a user or users define an insertion point and make a trajectory, then the one or more users may put the guidance device 105 on the insertion point of the patient. The guidance device 105 may be fixed to the patient using any known methods or tools to those skilled in the art, including, but not limited to, using sticky tape. Thereafter, the patient may be scanned by the image scanner 5 (e.g., a CT scanner) with the guidance device 105 in place on the patient.

In one or more embodiments, at least the first processor 1201 registers the guidance device 105 and the scanned images using the fiducial markers 209. The first processor 1201 is able to detect a position of the guidance device 105 in 3D space because the fiducial markers 209 are placed in the fixed part or portion 205 of guidance device 105 (see e.g., FIG. 2). Alternatively or additionally, registration may be performed using the other structural configurations and/or methods discussed herein, or may be set by using data defining a predetermined location/position as aforementioned.

After the guidance device 105 is registered, the first processor 1201 may update the trajectory automatically to reduce error (or a user may update the trajectory manually via interaction with the first processor 1201 when desired). To avoid errors that may occur in a situation where a center of the guidance device 105 is different from a predefined insertion point, in one or more embodiments, the first processor 1201 may update the insertion point to set the center of the guidance device 105, and may calculate the insertion angle and depth thereafter.

In one or more embodiments, the first processor 1201 may send insertion angle information, and may enable a signal of one or more guidance features to the guidance device 105 (e.g., before the guidance device 105 beings to guide the one or more needles and/or other medical apparatus attached thereto for guidance). After the one or more guidance features of the guidance device 105 are enabled, the LEDs or other indicators of the device 105 may be lit or turned on to indicate information for the user or users. The guidance device 105 may begin guidance when target angle information is received. Then, an enable or disable signal may not have to be used in one or more embodiments as aforementioned.

In at least one embodiment, as best seen in FIG. 9A, the second processor 1201' may read the angle information and the status information from the encoder sensor 203 cyclically, and may transmit the angle information and the status information to the first processor 1201 cyclically. In one or more embodiments, both frequencies may be different and/ or do not have to be the same. In one or more embodiments, the second processor 1201' may calculate a difference between each angle information and target angle during guidance. The second processor 1201' may control the LEDs (such as, but not limited to, the illumination indicator 2174a, the illumination indicator 2174b, the aforementioned three LEDs (e.g., a center or middle LED and the other two LEDS used for angle detection/guidance), etc.) based on the difference and status. LEDs may alternatively be replaced by other types of illumination or visual indicators (e.g., different color indicators, different shape indicators, etc.). The first processor 1201 preferably monitors received information, and may operate to show any errors on the display 1209 to notify the user or users of a situation where the first processor 1201 has detected or found any errors. The first processor 1201 may detect errors by itself or on its own. As shown in FIG. 9A, the first processor 1201 may disable the one or more guidance features of the device 105 in a case where one or more of the following (or any combination of the following) is/are satisfied: angle information and a target angle are matched or substantially near each other; angle information is stable; and/or the user or users abort the guidance. The guidance device 105 operates to continue guidance (and to not stop guidance) when one or more troubles occur regarding the wireless connection between the one or more components of the system 10 and the guidance device 105.

In at least one embodiment, as best seen in FIG. 9B, the first processor 1201 may enable guidance, and the second processor 1201' may read angle information from the encoder sensor 203 cyclically. However, in at least this embodiment, a difference exists in that the second processor 1201' does not need to transmit the angle information and the status information to the first processor 1201. The second processor 1201' may calculate the difference between each angle information and target angle during guidance, and the second processor 1201' may control the LEDs (such as, but not limited to, the illumination indicator 2174a, the illumination indicator 2174b, the aforementioned three LEDs (e.g., a center or middle LED and the other two LEDS used for angle detection/guidance), the LEDs 210 of FIG. 1, etc.) based on the difference and status as aforementioned. As an additional difference, the second processor 1201' may stop the one or more guidance features by itself in a case where one or more of the following (or any combination of the following) is/are satisfied: the angle information and the target angle are matched or substantially near each other; the angle information is stable; and/or the user or users abort the guidance. Once guidance is completed, the second processor 1201' may send a guidance completion signal or information to the first processor 1201. The guidance device 105 operates to continue guidance (and to not stop guidance) when one or more troubles occur regarding the wireless connection between the one or more components of the system 10 and the guidance device 105.

Additionally, in one or more embodiments, the first processor 1201 may reconstruct an oblique image based on loaded images and angle information. The first processor 1201 may show the image on the display 1209, and may update the displayed image to be synchronized with new angle information.

In a case where the medical procedure is ablation for example, the method(s) may include one or more ablation planning and performance steps, including, but not limited to, one or more of the following: (i) loading images (e.g., from a scanner, a PACS or other scanning device/system, or using a fresh or newly scanned image) (see step S1 in FIG. 10); (ii) visualizing images (e.g., such as by showing multiple panes (views, such as, but not limited to, axial, coronal, sagittal, 3 dimensional (3D), etc.) (e.g., each view may represent a different aspect of an image (e.g., a CT DICOM image); showing at least one pane of an image; loading an image (e.g., a CT DICOM image) and displaying it on a computer for visualization purposes; allowing a user to interact with a displayed image in one or more panes by moving at least one line (e.g., an axis or axes) to cut through one or more planes to reformat a 3D data set and display the reformatted slices in the 3D view; etc.)) (see step S2 in FIG. 10); (iii) identifying a treating zone or target (e.g., a lesion or tumor) (see step S3 in FIG. 10); (iv) defining a target point, an entry point and a trajectory between the target and entry points (see step S4 in FIG. 10) (as shown in step S4b, Step S4 may include repeating the process if there is one trajectory or there are multiple trajectories (and multiple target points) depending on a characteristic of a tumor or lesion); and (v) correspond the entry point in a particular image to an entry point for a body of the patient (see step S5 in FIG. 10). Determination of the target points (and the number of target points) may be at the discretion of the clinicians in one or more embodiments, or may be dependent upon the characteristic(s) of the target biological object, such as a lesion or tumor (e.g., a size of the lesion or tumor, a shape of the lesion or tumor, etc.). In one or more embodiments of the present disclosure, a method is provided to determine or suggest a target point or points that is clinically the best choice (e.g., mathematically, statistically, etc.) for placement of the target point(s). In one or more embodiments, target point(s) may be determined by finding or determining a medial axis or center line of the target or treating zone (see step S4 of FIG. 10).

Figure 10:
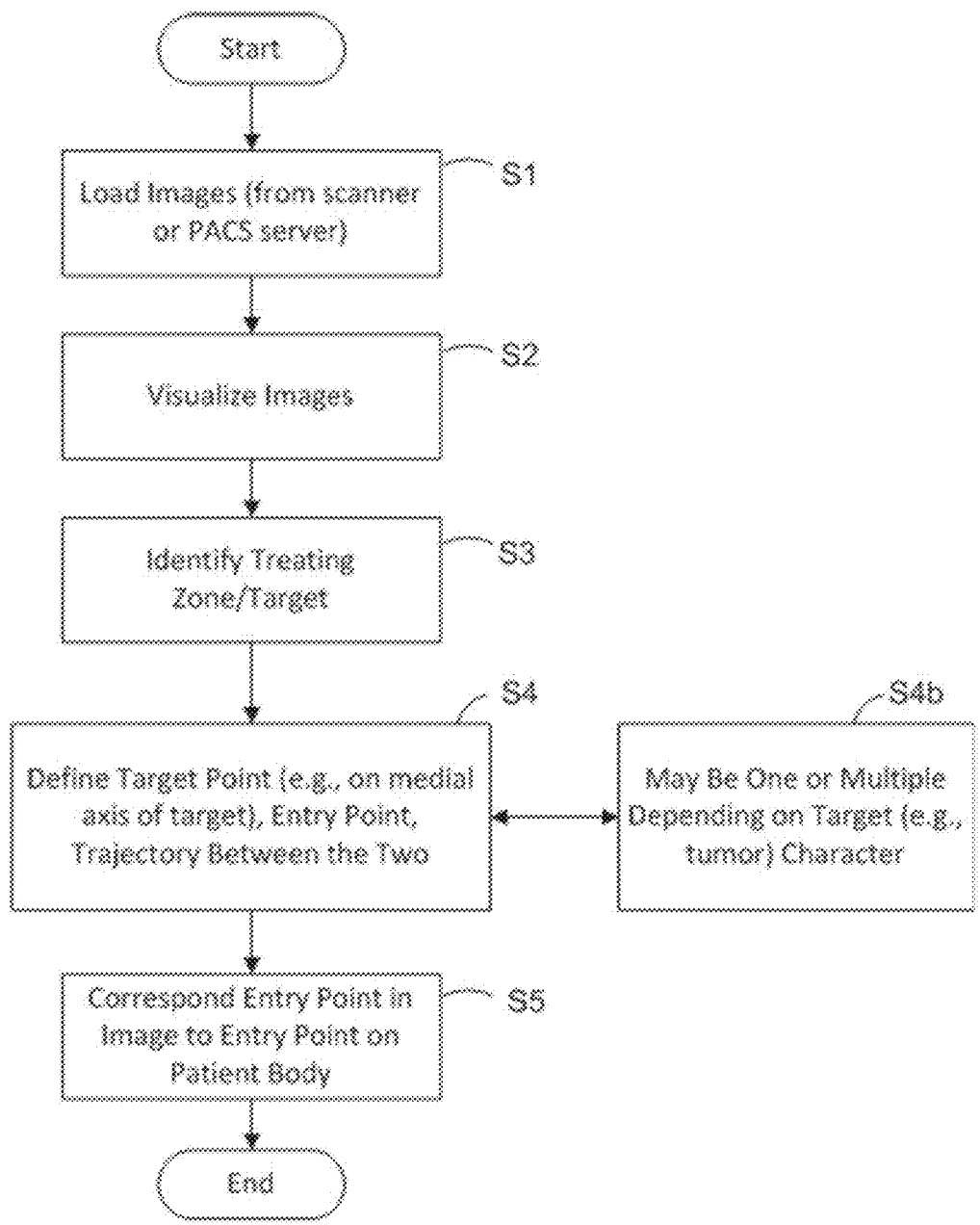
FIG. 10 is a flow chart showing at least one embodiment of a method for performing ablation and/or needle guidance planning and/or performance in accordance with one or more aspects of the present disclosure.
Figure 11:
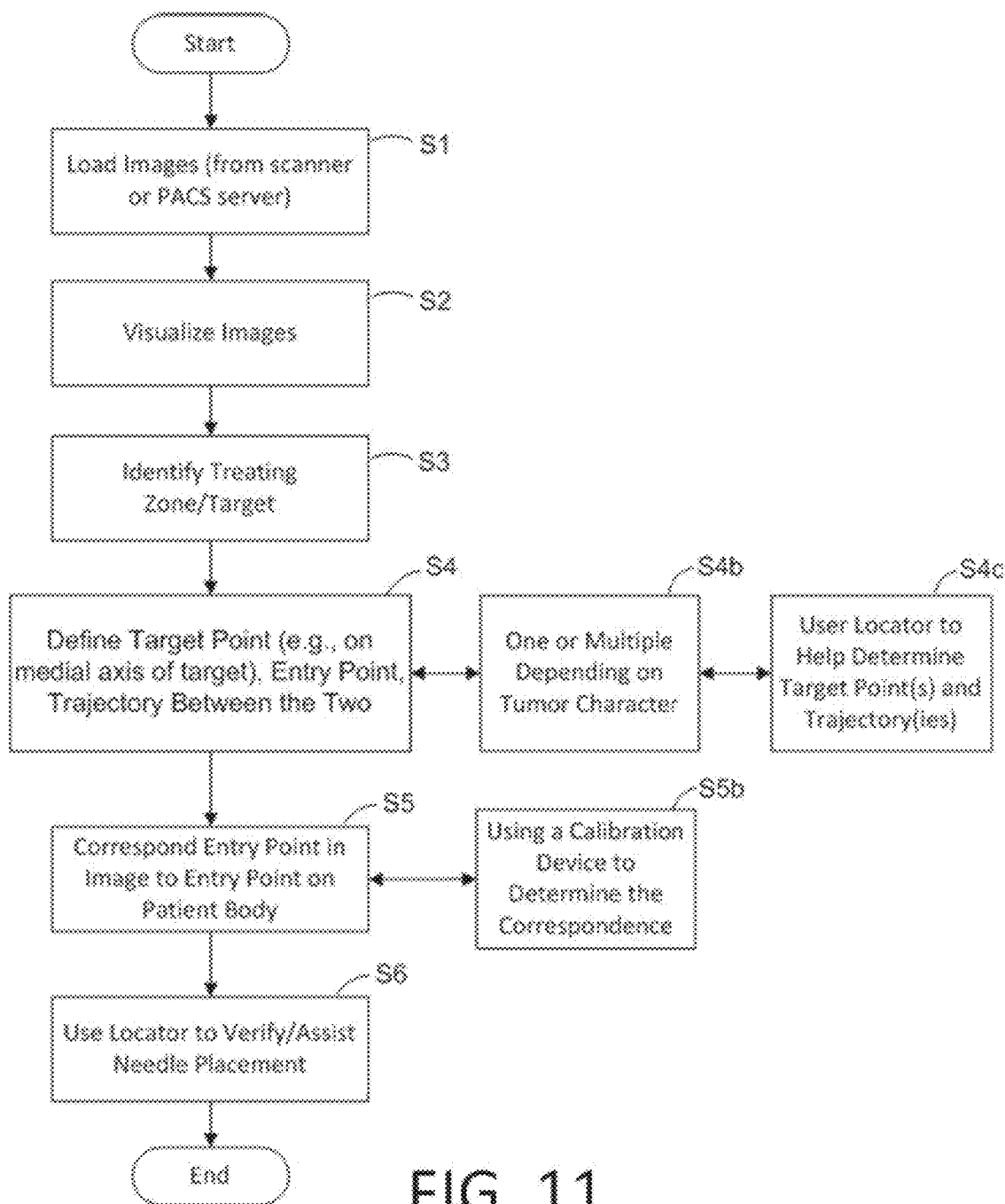
FIG. 11 is a flow chart showing at least another embodiment of a method for performing ablation and/or needle guidance planning and/or performance in accordance with one or more aspects of the present disclosure.

For any identification of a target or targets step(s) discussed herein (such as, but not limited to, step S3 of FIGS. 10-11; step(s) S4, S4b of FIG. 10; step(s) S4, S4b, S4c of FIG. 11; etc.), any method of identifying a target biological object or zone, including those known to those skilled in the art, such as a clinician, and including the additional method(s) provided herein, may be employed. For example, in one or more embodiments, a target zone and target points are to be identified. A target zone may be identified by an image segmentation method(s). Clinicians may initially define a few points, called seeds, which may or may not be the target points within an identified a target region, such as a lesion or tumor region. In one or more embodiments, an active contour model, such as a snake algorithm (see e.g., one example explained by C. Xu and J. L. Prince in "Gradient Vector Flow: A New External Force for Snakes", Proc. IEEE Conf. on Comp. Vis. Patt. Recog. (CVPR), Los Alamitos: Comp. Soc. Press, pp. 66-71, June 1997), may be used to iteratively determine a boundary of the target region. The initial seeds may not converge to a true boundary quickly, so, in one or more embodiments, a watershed method (see e.g., one example explained by Gouze A., De Roover C., Herbulot A., Debreuve E., Barlaud M., Macq B. in "Watershed-driven Active Contours for Moving Object Segmentation", in Proceedings of IEEE International Conference on Image Processing (ICIP), vol. II, pp 818-821, Genova, Italie, September 2005) may be used together with the snake algorithm to make the segmentation smoother and faster. Compared to manually drawing a boundary of a target region, such as a lesion or tumor region, such a method or methods generate a far more accurate and consistent boundary, which may be used to determine a volume of a target (e.g., a tumor or lesion) and may be used in a later stage for quantitatively characterizing the tumor or lesion and assessing ablation results. The resulting boundary forms a target zone.

Additionally or alternatively, one or more method(s) of the present disclosure may further include performing ablation planning and/or performance with the guidance device 105 as shown in FIG. 6. In addition to the steps shown in FIG. 10 (the details of which are aforementioned and will not be repeated herein accordingly), such one or more method(s) employing a guidance device, such as the guidance device 105 may further include, but are not limited to, one or more of the following: (i) using a guidance device, such as the guidance device 105, to help determine the target point(s) and trajectory(ies) in steps S4 and/or S4*b* (see also steps S4, S4*b* and S4*c* in FIG. 11); (ii) using a calibration device (e.g., such as, but not limited to, fiducial markers (e.g., the fiducial markers 209), systems and methods of registration, such as those disclosed in U.S. patent application Ser. No. 14/755,654 and published in U.S. Pat. Pub. No. 2017/0000581, which are incorporated by reference herein in their entireties) to determine or assist with the correspondence step of S5 (see also steps S5 and S5*b* in FIG. 11); and (iii) using a guidance device, such as the guidance device 105, to verify and/or assist with needle placement when performing ablation for the patient (see step S6 in FIG. 11). In one or more embodiments of the present disclosure, at least one embodiment of a method for performing ablation planning or ablation performance is to use such calibration device(s) and/or locator device(s) to increase or maximize the success of the ablation procedure depending on one or more variables, such as, but not limited to, needs of the patient, characteristics of the lesion/tumor, if movement of the patient is needed during the procedure, etc. In one or more embodiments of the present disclosure, such calibration device(s) and/or locator device(s) assist a clinician in finding a medial axis or center line of the target biological object, such as a lesion or tumor.

In one or more embodiments, workflow for a particular procedure, such as needle guidance planning and/or performance and/or ablation planning and/or ablation performance, may be combined with segmentation, registration and differential image view steps to provide better differential images (such as, but not limited to, segmentation, registration and differential image steps disclosed in PCT/US2018/020752, which is incorporated by reference herein in its entirety), which avoid the generation of misleading artifacts in images and/or avoid other issues with procedure-related problems. Differential images are a quick way to give clinicians feedback of needle guidance and/or ablation results. While thermal maps may be used in one or more embodiments, such thermal maps may be affected by environmental changes, such as blood flow, and measurements may not be easily localized depending on the circumstances. Various types of ablation may be used in one or more embodiments (e.g., cryoablation, microwave ablation, laser ablation, etc.). While cryoablation may be used, iceballs may form, and are very visible under MRI. Ultrasound may be used in one or more of the methods discussed herein for navigation, and some indication of an ablation result may be obtained from the same tool. However, ultrasound images may be noisy and may be hard to quantitatively measure. Regardless of which detection or monitoring tool/technique is employed, the integration of the workflow with segmentation, registration and differential image view steps reduces and/or avoids such issues to provide a useful differential image or images for clinicians to use in one or more procedures (e.g., ablation, radiotherapy, etc.).

For medical procedures, such as ablation, one probe ablation or multi-probe ablation may be performed. For multi-probe ablation, serial or parallel multi-probe ablation may be performed. In serial ablation, ablation is done in sequence of one probe being inserted, ablated, confirmed, then another probe being inserted, ablated, confirmed, and repeating such steps if more probes are needed. In parallel ablation, all probes are inserted before ablation starts. Clinicians may decide which ablation approach is chosen. No matter which approach is chosen, a confirmation stage is needed after the ablation is done. Based on information from each confirmation, a clinician may determine whether additional ablation is needed, and, if so, where to plan for the next probe to be used. Confirmation also provides clinicians with an indication as to whether the margin is reached or overreached to evaluate the results of the ablation procedure.

To aid clinicians in performing confirmation steps, one or more embodiments of the present disclosure may include confirmation with margin view so that confirmation or any other determination process requiring clear image feedback may be performed more effectively (such as, but not limited to, confirmation steps disclosed in PCT/US2018/020752, which is incorporated by reference herein in its entirety). While quantitative measure of coverage is useful, a visual quick assessment is also very useful in one or more applications. The margin view gives a better view than the common overlay of before and after ablation images to more easily and effectively determine the success of the ablation process. In one or more embodiments, the target(s), such as lesion(s) or tumor(s) may be segmented before and after ablation occurs, and differentiation between the two sets of segmented target images may be determined. Thereafter, the differential may be overlaid on the after-ablation images to evaluate the ablation process. Additionally or alternatively, one or more method(s) of the present disclosure may further include performing ablation planning and/or performance with the guidance device 105 as shown in FIG. 6 and in FIGS. 10-11. One or more embodiments of methods for evaluating or determining a margin view may include, but are not limited to, one or more of the following: (i) loading images (e.g., from a scanner, a PACS or other scanning device/system, or using a fresh or newly scanned image) (see step S1 in FIGS. 10-11); (ii) visualizing images (e.g., such as by showing multiple panes (views) (e.g., each view may represent a different aspect of the image); as described above for step S2 in FIGS. 10-11; (e.g., in medical image software, such as, for example, the application shown in PCT/US2018/020752, which is incorporated by reference herein in its entirety); as otherwise described herein; etc.)

(see step S2 in FIGS. 10-11); (iii) performing device registration (also referred to herein as device calibration) to make a correct correspondence or alignment between an image and real world dimensions for a patient (see e.g., steps S5 and/or S5b of FIG. 10o and/or FIG. 11 which may be incorporated into or used as a configuration or registration step; see also, device registration as discussed in PCT/US2018/020752, which is incorporated by reference herein in its entirety); (iv) identify a target or target(s), such as a zone or biological object (see step S3 of FIGS. 10-11); (v) segmenting the identified targets (at one reference point in the planning or procedure (e.g., before moving a needle, before performing ablation, before performing the next iterative or incremental planning step (either during the procedure or in simulation or planning), before moving a patient, etc.)—also referred to herein as "targets (1)", i.e., the targets identified at stage (1)); (vi) performing an incremental planning or performance step (e.g., move a needle, insert a new probe or needle, perform ablation, perform the next planning step, moving a patient, etc.); (vii) re-scanning the targets or obtaining newly scanned images of the targets after performing the incremental planning or performance step; (viii) visualizing images (e.g., such as by showing multiple panes (views) (e.g., each view may represent a different aspect of the image); as described above for step S2 in FIGS. 10-11; as otherwise described herein; etc.)); (ix) identifying a target or target(s), such as a zone or biological object (which may be the same or similar to step S3 of FIGS. 10-11 such that the above details regarding same are not repeated herein); (x) segmenting the re-scanned targets (at a second reference point in the planning or procedure (e.g., after moving a needle, after moving or adding a probe, after performing ablation, after performing the next iterative or incremental planning step (either during the procedure or in simulation or planning), etc.)—also referred to herein as "targets (2)", i.e., the targets as re-scanned at stage (2) after stage (1)); (xi) performing image registration (e.g., before conducting differentiation of current images and previous images); (xii) performing differentiation of current images (e.g., images of stage (2)) and previous images (e.g., images of stage (1)) to enhance the view of the effect of the procedure (e.g., ablation (especially when using microwave or radiofrequency (RF) ablation (in one or more embodiments, differentiation subtraction may not be needed for cryoablation)), radiotherapy, etc.); and (xiii) overlaying the differential on the current images (e.g., images of stage (2)). Image segmentation and registration may be performed using any method known to those skilled in the art, such as a clinician.

The image differentiation may be used to enhance the visualization of a needle guidance result and/or an ablation result, monitor probe progression during insertion, or to track any other incremental step in a procedure (e.g., ablation, radiotherapy, etc.). By way of example, a concept of such an enhancement after performing ablation is shown in PCT/US20018/020752, which is incorporated by reference herein in its entirety. The target or target zone of a biological object (such as a lesion or tumor) is surrounded by an ablation zone or ablated zone (once ablation is performed). As such, in one or more embodiments, such as when performing differentiation and overlaying the differential on the current image(s) of stage (2) or final images, a margin map is formed. The margin map may be used by a clinician to determine whether or not to edit a procedure plan and/or to evaluate whether the plan or procedure is optimal (e.g., the best option available) or has been successful (and to gauge how successful). This improved ability to measure success is good for feedback (such as for the clinician, patient, hospital, other clinicians consulting such results, etc.), and provides an outcome oriented application in one or more embodiments of the present disclosure. For example, the percent of the margin (and/or other metrics of the margin) may be used to indicate how well the procedure went. A minimum or a maximum of the margin view or map may be set or predetermined by a clinician. The treatment or target zone may be displayed, overlaid on the target zone or target object (segmented), e.g., a tumor or lesion.

Additionally or alternatively, clinicians may perform simulations with one or more embodiments of the planning methods/software of the present disclosure to create an optical plan, to accommodate one or more variables (e.g., patient movement during the procedure, tissue deformations, etc.), and to evaluate the potential outcome. By way of at least one example, a simulation of a target zone (e.g., in an example where the medical procedure is ablation, the simulation may be an ice ball for cryoablation, a balloon for microwave ablation, etc.) may be conducted. By way of another example, a simulation may be performed to mimic tissue deformation. For example, if clinicians segmented an organ or tumor (suppose an oval shape for purposes of the example simulation), the medial axis algorithm may take the segmented object as input and generate a medial axis output (typically it is a curve), which may be overlaid on the segmented object. By dragging and manipulating the medial axis curve, the curve may change its shape and location in space. Due to the fact that a volume may be reconstructed from a medial axis curve, the deformation may be simulated or obtained by dragging and manipulating the medial axis.

One or more embodiments of the needle guidance planning and performance apparatuses and systems, and methods and storage mediums of the present disclosure may operate to reduce the number of iterations for the determination of the insertion point(s) and trajectory of the needle(s) and/or probe(s) after being inserted into the entry point(s). This is beneficial for reducing exposure to radiation when dealing with CT scans and reduces the total time of scanning when dealing with any type of scan, including, but not limited to, CT, MRI or otherwise. In one or more embodiments, registration with fiducial markers (such as a sticker grid as aforementioned, the fiducial markers 209, etc.) may be used on the patient at or near an insertion point before conducting a CT/MRI scan. This registration step helps to accurately correlate physical dimensions to what to see in the scanned images.

After a target zone is identified, clinicians may pick up a point or a few points within the target zone as target point(s). From there on, in the case of ablation, an ablation zone (for example iceball) may be defined on or around the target zone (e.g., in the case of the iceball example, the ball may be centered on the ablation zone). In other medical procedures, a guidance zone for one or more needles may be more generally defined on or around the target zone.

While clinicians may pick target points by trial and error, such trial and error leads to inefficiencies, such as, but not limited to, longer procedure time, more invasive and repeated steps (e.g., needle or probe insertion/movement), lack of accuracy, etc.

Figure 12:
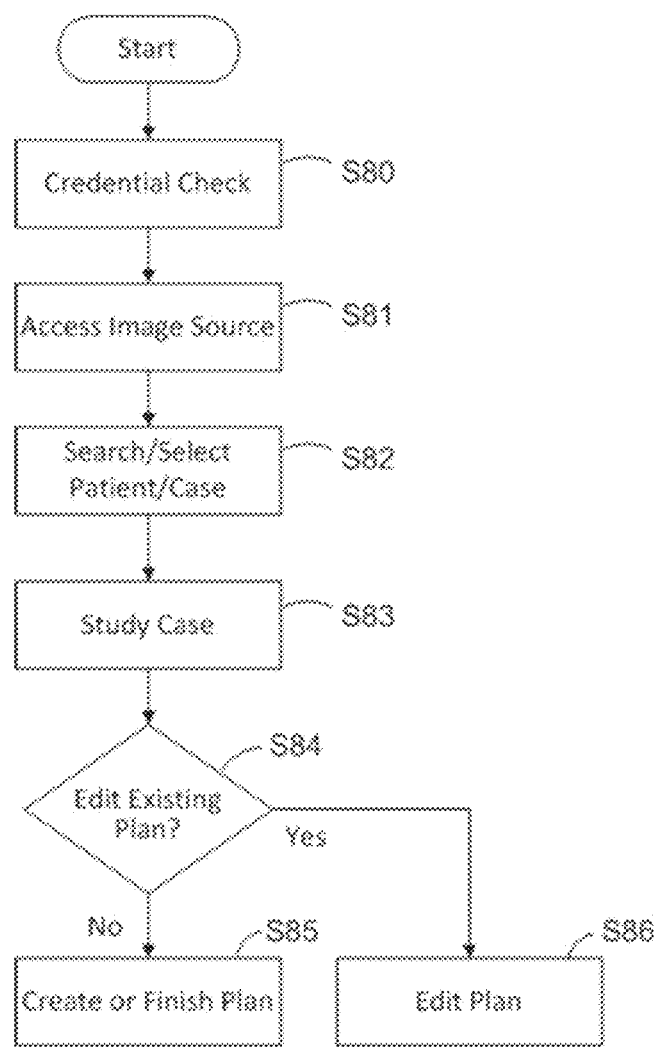
FIG. 12 is a flow chart showing at least another embodiment of a method for performing a medical procedure (e.g., ablation and/or needle guidance planning and/or performance) using a security or credential check in accordance with one or more aspects of the present disclosure.

Additionally, in one or more embodiments, a security check may be included to perform the check in the surgical room prior to the needle guidance planning and/or procedure to ensure maximal security and safety. To make the security check convenient for clinicians (who have scrubbed in and are wearing gloves at that point and may not be able to use their hands for performing the security check), iris and/or face recognition may be incorporated. Such iris and/or face recognition based approaches may be preferred to control access to patient data (CT scan for example) and communication with peers. While other forms of security control may be used, forms, such as, but not limited to, typing a password, finger print scan, or other forms that require the use of a clinician's hand(s), may not be preferred because a clinician's hands may be sterilized. Once logged in, clinicians may be able to access patient data and communication with peers. FIG. 12 depicts where this checking step may be employed for access image data to create or edit a plan for any medical procedure, such as ablation, cryotherapy, biopsy, etc. For example, prior to any method disclosed herein for performing needle guidance planning and/or performance or ablation planning and/or performance, the credential check (step S80 of FIG. 12) may be performed to make sure that the clinician is permitted to access patient data and communication with other clinicians. Once the clinician passes the credential check (S80), then the clinician has access to the image source (see step S81 of FIG. 12), and may search or select a patient or case file (see step S82 of FIG. 12). Once the patient or case file is retrieved in step S82, the clinician may study the case (see step S83 of FIG. 12), and may determine whether edit(s) to an existing procedure plan (e.g., an ablation plan, a radiotherapy plan, a biopsy plan, needle guidance plan, etc.) are required or not (see step S84 in FIG. 12). If "No" edits to an existing plan are needed (e.g., a plan is finished, a plan does not exist, etc.), the clinician may create or finish a plan for the procedure (see step S85 of FIG. 12). If "Yes" and edits to an existing plan are needed, the clinician may edit the previously created plan (see step S86 of FIG. 12). These steps may be used in addition to any of the aforementioned methods for performing needle guidance planning and/or performance, for ablation planning and/or ablation performance, for radiotherapy planning and/or performance, for guiding multiple needles or multiple ablation probes, or other procedural methods as may be useful.

Figure 13:
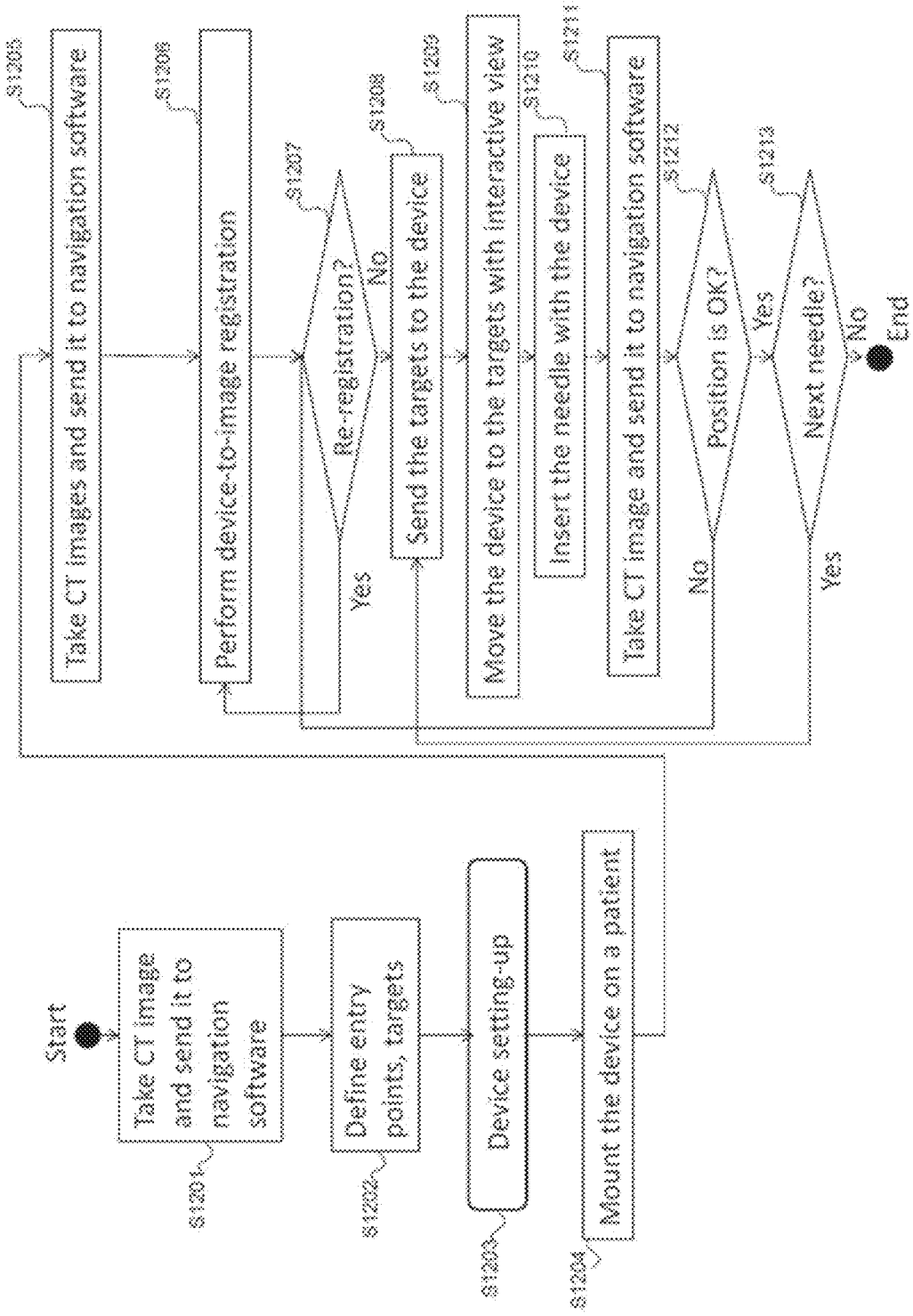
FIG. 13 is a flow chart illustrating a process for guidance of a needle using a medical guidance device and/or system in accordance with one or more aspects of the present disclosure.

FIG. 13 is a flowchart illustrating a process for guidance of a needle or needles using the medical guidance device 105. In step S1201, an operator takes medical images using the medical imaging device 5. The medical imaging device 5 is a CT scanner in this particular embodiment, and sends the CT images to the first processor 1201 of the computer 2 as aforementioned.

At step S1202, with the CT images, the operator defines targets for percutaneous intervention with a needle-like medical tool and the skin entry point. At the same time, by connecting the target to the skin entry point, the operator can determine the plane for the trajectory of insertion of the needle-like medical tool using at least the first processor 1201 (and any images and/or software displayed on the aforementioned display 1209 of the computer 2). Also, in this step, the operator marks the skin entry point on the patient using, for example, grid visible markers on the patient as aforementioned.

In step S1203, the operator sets up the system 10, including the device 105, to calibrate the system 10 and/or one or more components thereof, and sets a proper initial state of the medical guidance device 105. Additionally, the first processor 1201 may set up, synchronize and/or otherwise figure out the orientation between the encoder sensor 203 and the encoder scale 204.

After the setting up the device 105, in Step S1204, the operator mounts the medical guidance device 105 onto the patient aligning a predetermined portion (e.g., a center) of the device 105 to the skin entry point. When an adhesive marker is being utilized, the operator may align a center marker to the skin entry point and then adhere the medical guidance device 105 in place via an adhesive. In one or more embodiments, the user then may remove a peel-away portion of the adhesive marker to expose the patient's skin.

In Step S1205, after the device mounting, the user takes images (e.g., CT images) including the medical guidance device 105 and sends the CT images to the first processor 1201 (and related navigation or guidance software for processing the data as needed). Using the CT images with the medical guidance apparatus 105 showing, in Step S1206, the user conducts device-to-image registration. In this step, the first processor 1201 (e.g., using guidance or navigation software) recognizes the position and orientation of the medical guidance device 105 on the patient in the CT images, i.e., in the coordinate of the CT image, by using fiducial markers (e.g., the fiducial markers 209) or fiducial markers located on the corners of the base ring 112 (the base ring 112 of the embodiment, for example, shown in FIGS. 4A-4B). This fiducial marker detection may be manually performed by user instruction with a user interface or, may be fully automated by using a computer algorithm via the first processor 1201 and/or the second processor 1201'. The detected fiducial markers are compared with the designed geometrical configuration of the fiducial markers in the medical guidance device 105, then the first processor 1201 and/or the second processor 1201' (e.g., using guidance or navigation software) may recognize the position and the orientation of the medical guidance device 105 in CT images. The navigation software may also reflect the plan of the trajectory with two device parameters, which are angular position of the moveable ring 120 ($\theta_E^F$) and insertion angle on guide 150 ($\theta_E^F$) at this step.

In step S1207, the user may be asked whether the device-to-image registration is appropriate or not by the first processor 1201 and/or the second processor 1201' (e.g., via the navigation software displayed on the display 1209). If not ("No" in Step S1207), the operator may conduct Step S1206 to perform the device-to-image registration again.

If the device-to-image registration is appropriate ("Yes" in Step S1207), flow proceeds to Step S1208 where the user may send the target device parameters $\theta_E^F$, $\theta_P^{MR}$ to the first processor 1201 and/or the second processor 1201'.

Afterwards in Step S1209, the operator may manually rotate the guide 150 via the moveable ring 120 and/or the movable portion 206 of the device 105 while the first processor 1201 and/or the second processor 1201' (e.g., using guidance or navigation software) interactively updates the cross-sectional image on the guide surface by using the real-time angular position of the moveable ring 120 or the movable portion 206. Also, the first processor 1201 and/or the second processor 1201' may compare the real-time angular position of the moveable ring 120 and/or the movable portion 206 with the target angular position. Once the moveable ring 120 or the movable portion 206 reaches the target angular position, the first processor 1201 and/or the second processor 1201' indicates the end of targeting of the moveable ring 120 or the movable portion 206 of the device 105. Then, the first processor 1201 and/or the second processor 1201' (e.g., via guidance or navigation software displayed on the display 1209) informs the user of the end of targeting or guidance.

Upon establishing the target angular position of the moveable ring 120 (and thereby the guide 150) or the movable portion 206 of the device 105, in Step S1210, the user picks the specific angular reference mark 174 (or other indicator mark being used in any particular embodiment) indicated by the target insertion angle on guide 150 or on the arc 207 of the device 105 and with the specific angular reference mark 174 (or other indicator), the user inserts the needle-like medical tool from the skin entry point to the target. In the case of the medical guidance apparatus device 105 (see various embodiment examples in FIGS. 1-6), the operator may slide the needle-like medical tool along the guide surface 172 (see FIGS. 3-4B) or the arc 207 (see FIGS. 1-2) until reaching the appropriate reference mark 174 (or other used marker). In doing so the user may apply force. However, due to the structural advantages discussed above provided by the closed/monolithic structure of the guide 150 and/or of the movable portion 206 of the device 105, the arc member 154 or the arc portion 207 is able to fully support the force without deflection or bending. In the case where the guide 2150 (FIG. 5A) is being used, the user may pass the needle-like medical tool through the instrument holder 2157. The user may then move the needle-like medical tool along the rail 2155 via the instrument holder 2157 until arriving at the appropriate marker indicator 2174*a* (or marker in the case of a marker being present). The guide surface 2172 also has the structural advantages noted above. Variations may be made to the device 105 in accordance with one or more features of the present disclosure. For example, other types of guidance devices 105 may be used, such as those discussed in U.S. Provisional Patent Application No. 62/764,849, filed on Aug. 15, 2018, and U.S. patent application Ser. No. 16/539,769, filed Aug. 13, 2019, which applications are incorporated by reference herein in their entireties.

In Step 1211, after the first attempt of the insertion, the user takes CT images of the inserted needle-like medical tool, the medical guidance device 105, and the CT images and sends them to the first processor 1201 and/or the second processor 1201' (and any guidance or navigation software being used). With the CT images of the inserted needle-like medical tool, the user evaluates the position of the inserted needle-like medical tool.

In step S1212, the position of the inserted needle-like medical tool is checked and if the user thinks the position is suboptimal ("No" in Step S1212), flow proceeds back to Step S1208 where the user can update the trajectory to improve the position of the needle-like medical tool with the first processor 1201 and/or the second processor 1201' (e.g., by using guidance or navigation software such as discussed in U.S. Provisional Patent Application No. 62/764,849, filed on Aug. 15, 2018, and U.S. patent application Ser. No. 16/539,769, filed Aug. 13, 2019, which applications are incorporated by reference herein in their entireties). At the same time, with the latest CT image, the user finds the dislocation of the target, skin entry point and the medical guidance device 105 and updates the registered position and orientation of the medical guidance device 105. Thus, the user can conduct the device-to-image registration with the latest CT images. By updating the device-to-image registration, the user can reduce discrepancy of the actual geometrical relationship between the medical guidance device 105 and the target. Specifically, since the medical guidance device 105 is mounted on the patient and can move with the patient body together, the update of the device-to-image registration can effectively compensate rigid dislocation of the patient from the older CT images.

With updated plane of the trajectory and the device-to-image registration, the user can perform another attempt of the insertion with the same steps as in the first attempt.

In step S1212, if the position of the inserted needle-like medical tool is checked and the user is satisfied with the results ("Yes" in Step S1212), flow continues to Step S1213. In Step S1213, a determination is made as to whether insertion of another needle-like medical tool is needed. If insertion of another needle-like medical tool is needed ("Yes" in Step S1213) flow returns back to Step S1205. If insertion of another needle-like medical tool is not needed ("No" in Step S1213) flow is complete. When inserting another needle-like medical tool, the user may decouple the guide 150 from the base assembly 110 or the movable portion 206 from the fixed portion 205 as necessary without needing to unmount the base assembly 110 or the fixed portion 205 of the aforementioned embodiment examples of the device 105. In the case of inserting another needle-like medical tool in another guide (such as the guide 2150, for example), preferably the user may remove the previous needle-like medical tool from the instrument holder 2157.

Once all of the needle-like medical tools have been inserted, the operator may decouple the guide 150 from the moveable ring 120. Once the guide 150 has been decoupled and can be freely lifted away, the operator may orient the guide 150 such that each of the needle-like medical tools passes through the gap 170. Thus, the guide 150 is completely removable from the procedure site, even when the needle-like medical tool is tethered, such as for percutaneous ablation probes. Similarly, one or more portions of the other embodiments of the device 105 may be removed as needed (e.g., the movable portion 206) as aforementioned.

In at least one embodiment, the computer 2, 2' operates to control the medical procedure (e.g., needle guidance, ablation, biopsy, etc.) planning and/or performance and/or probe or needle guidance device(s), system(s) and/or storage medium(s), and may display the scanned image(s) and the procedure plan (e.g., on a monitor or screen such as a display, screen or monitor 1209 as shown in the computer 2 of FIG. 6, in the computer 2 of FIG. 14 and/or the computer 2' of FIG. 15 as further discussed below). The console or processor 2, 2' (or the first processor 1201 of the console or computer 2, 2') or the second processor 1201' of the device 105 may be used to control any portions of the system 10 of FIG. 6, for example, including, but not limited to, the medical device 1, the guidance device 105, the PACS system 4, the image scanner and console 5 (e.g., CT scanner), etc. The processor 1201 of the console 2, 2' and/or the second processor 1201' of the device 105 may be used to perform any of the aforementioned method(s) or algorithm(s), and may use one or more feature(s) of such method(s) or algorithm(s) in any combination desired by a clinician for a predetermined procedure (e.g., medical procedure (e.g., ablation, biopsy, etc.) planning and/or performance; needle or probe guidance; a combination thereof; etc.). For example, the CPU 1201 of the processor 2, 2' may load images (e.g., from a scanner or PACS 4) in step S1 of FIGS. 10-11, and may display such images to allow the clinician to visualize the images (e.g., in step S2 of FIGS. 10-11). The computer, such as the console or computer 2, 2', may receive data from a device (e.g., such as the guidance device 105, an image scanner 5, a PACS 4, etc.) or a system via a network interface (see e.g., communication interface 1205 and network 1206 as shown in FIG. 14 or Network I/F 1212 as shown in FIG. 15), or the computer, such as the console or computer 2, 2', may obtain a set of imaging conditions using the operation input from the mouse or keyboard (see e.g., the keyboard 1210 as shown in FIG. 14 or the mouse 1211 and/or keyboard 1210 as shown in FIG. 15).

Unless otherwise discussed herein, like numerals indicate like elements. For example, while variations or differences exist between the methods, devices, systems or storage mediums, such as, but not limited to, the system 10, the communication sequences and methods shown in FIGS. 9A-13, etc., one or more features thereof may be the same or similar to each other, such as, but not limited to, the use of one or more component(s) thereof (e.g., the console 2, the console 2', the medical device 1, the guidance device 105, the PACS 4, the CT scanner 5, any or all of the components of FIGS. 1-9B, etc.). Those skilled in the art will appreciate that the method steps disclosed herein may operate in the same or similar fashion to those like-numbered elements of one or more other methods or algorithms as discussed herein. Those skilled in the art will appreciate that alternative embodiments of the system 10, may be used while having other variations as discussed herein for performing one or more methods discussed herein. Likewise, while the console or computer 2 may be used in one or more systems or with one or more methods disclosed herein, one or more other consoles or computers, such as the console or computer 2', may be used additionally or alternatively.

There are many ways to plan for and perform a medical procedure (e.g., needle guidance, ablation, biopsy, etc.) or any other measurement or determination discussed herein, digital as well as analog. In at least one embodiment, a computer, such as the console or computer 2, 2', may be dedicated to control and monitor the devices, systems, methods and/or storage mediums described herein.

The electric signals used for imaging may be sent to one or more processors, such as, but not limited to, a computer or processor 2 (see e.g., FIGS. 6 and 14), the first and second processors 1201, 1201' (see e.g., FIG. 8), a computer 2' (see e.g., FIG. 15), etc. as discussed further below, via cable(s) or wire(s), such as, but not limited to, the cable(s) or wire(s) 119 (see FIG. 14). Additionally or alternatively, the electric signals, as aforementioned, may be processed in one or more embodiments as discussed above by any other computer or processor or components thereof. The computer or processor 2 as shown in FIGS. 6 and 14 may be used instead of any other computer or processor discussed herein (e.g., computer or processors 1201, 1201', 2', etc.), and/or the computer or processor 2, 2' may be used instead of any other computer or processor discussed herein (e.g., computer or processor 1201, 1201', etc.). In other words, the computers or processors discussed herein are interchangeable, and may operate to perform any of the multiple imaging modalities feature(s) and method(s) discussed herein, including using, controlling, and changing a GUI or multiple GUI's and/or performing one or more methods, including, but not limited to, wireless needle guidance method(s), discussed herein.

Various components of a computer system 2 (see e.g., the console or computer 2 as shown in FIG. 6) are provided in FIG. 14. A computer system 2 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 6). In addition, the computer system 2 may comprise one or more of the aforementioned components. For example, a computer system 2 may include a CPU 1201, a RAM 1203, an input/output (I/O) interface (such as the communication interface 1205) and a bus (which may include one or more lines 1213 as a communication system between components of the computer system 2; in one or more embodiments, the computer system 2 and at least the CPU 1201 thereof may communicate with the one or more aforementioned components of an ablation performance and/or planning and/or needle or probe guidance device or system, such as, but not limited to, the system 10 discussed herein above, via one or more lines 1213 or wirelessly through a first wireless circuit 1205, 1212 and a second wireless circuit 1205, 1212, and/or through communication or network interfaces that include wired and wireless structural attributes and features), and one or more other computer systems 2 may include one or more combinations of the other aforementioned components. The CPU 1201, 1201' is configured to read and perform computer-executable instructions stored in a storage medium. The computer-executable instructions may include those for the performance of the methods and/or calculations described herein. The system 10 may include one or more additional processors in addition to CPU 1201, and such processors, including the CPU 1201, may be used for performing ablation planning and/or performance and/or multiple needle or multiple ablation probe guidance. The system 10 may further include one or more processors connected via a network connection (e.g., via network 1206). The CPU 1201 and any additional processor being used by the system 2 or the system 10 may be located in the same telecom network or in different telecom networks (e.g., performing needle guidance, medical procedure (e.g., ablation, biopsy, etc.) planning and/or performance technique(s) may be controlled remotely or wirelessly).

The I/O or communication interface 1205 provides communication interfaces to input and output devices, which may include the medical device 1, the guidance device 105, the PACS 4, the CT scanner 5, a microphone, a communication cable and a network (either wired or wireless), a keyboard 1210, a mouse (see e.g., the mouse 1211 as shown in FIG. 15), a touch screen or screen 1209, a light pen and so on. The Monitor interface or screen 1209 provides communication interfaces thereto.

Any methods and/or data of the present disclosure, such as the methods for performing ablation planning and/or performance, radiotherapy, guidance of needle(s) and/or probe(s), or otherwise as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 15), SRAM, etc.), an optional combination thereof, a server/database, etc. may be used to cause a processor, such as, the processor or CPU 1201 of the aforementioned computer system 2 and/or the system 10, the second processor 1201' of the device 105, etc., to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 2, the processor 1201' of the device 105, etc., as described above may be achieved utilizing suitable hardware, such as that illustrated in the figures. Functionality of one or more aspects of the present disclosure may be achieved utilizing suitable hardware, such as that illustrated in FIGS. 1-9B, FIG. 14 and/or FIG. 15. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201, 1201' (as shown in FIGS. 8-9B, 14 and/or 15) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 2' is shown in FIG. 15. The computer 2' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 2' includes a display 1209. The computer 2' may connect with the medical device 1, the guidance device 105, the PACS 4, the CT scanner 5, communication devices (e.g., to discuss the procedure with peers, clinicians, etc.) via the operation interface 1214 or the network interface 1212 (e.g., via wired or wireless connection). The operation interface 1214 is connected with an operation unit such as a mouse device 1211, a keyboard 1210 or a touch panel device. The computer 2' may include two or more of each component.

In at least one embodiment, at least one computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 2, 2', communicates with one or more other system components (e.g., the medical device 1, the guidance device 105, the PACS 4, the CT scanner 5 or other type of scanner, of system 10 or other device or system being used for medical procedure (e.g., needle guidance, ablation, biopsy, etc.) planning and/or performance) to perform imaging, planning and/or performance. The monitor or display 1209 displays the plan and performance and/or guidance steps (e.g., in real time), and may display other information about the imaging condition or about an object to be imaged and operated on during the procedure. The monitor 1209 also provides a graphical user interface for a user to operate an ablation planning and/or performance and/or needle guidance or ablation (or other medical procedure) probe guidance device or system (e.g., the system 10). An operation signal is input from the operation unit (e.g., such as, but not limited to, a mouse device 1211, a keyboard 1210, a touch panel device, etc.) into the operation interface 1214 in the computer 2', and corresponding to the operation signal the computer 2' instructs the system (e.g., the system 10) to set or change the imaging, planning and/or performance condition(s), and to start or end any portion of any of the method(s) discussed herein.

The present disclosure and/or one or more components of devices, systems and storage mediums, and/or methods, thereof also may be used in conjunction with any suitable optical assembly including, but not limited to, ablation technology, such as in U.S. Pat. No. 9,867,673; U.S. patent application Ser. Nos. 16/027,093, 15/836,141, and 15/727, 978; U.S. Provisional Patent Application No. 62/764,849, filed on Aug. 15, 2018; U.S. Provisional Patent App. No. 62/764,820, filed Aug. 15, 2018; U.S. Provisional Patent App. No. 62/875,243, filed Jul. 17, 2019; U.S. patent application Ser. No. 16/539,769, filed Aug. 13, 2019; U.S. Pat. Pub. No. 2019/0105109, published on Apr. 11, 2019; U.S. Pat. Pub. No. 2019/0008591, published on Jan. 10, 2019; U.S. Pat. Pub. No. 2018/0098819, published on Apr. 12, 2018; App. No. PCT/US2018/020752; and App. No. PCT/US15/40336, each of which patent(s), patent publication(s) and application(s) are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. A medical guidance device comprising:
   a first portion including a portion defining an opening and including an encoder sensor, the first portion operating to be fixed to an object, a target, or a patient;
   a second movable portion that is removably and movably mateable with the first portion, the second movable portion including a portion defining an opening, the second movable portion operating to hold at least one medical tool to be guided by the medical guidance device, and the second movable portion including an encoder scale that operates to interact with the encoder sensor to achieve positional sensing between the first portion and the second movable portion; and one or more processors that operate to guide or navigate the at least one medical tool held in the medical guidance device and that operate to communicate with another processor wirelessly, wherein the opening of the first portion overlaps with, is co-planar with, or is parallel to, the opening of the second movable portion such that the at least one medical tool operates to pass through the opening of the first portion and the opening of the second movable portion to have access to the object, the target, or the patient, and wherein one or both of the first portion or the second movable portion include one or more of the following:

one or more illumination or visual indicators that operate to aid in the guidance of the at least one medical tool, and/or a guidance surface having one or more reference marks or a reference scale, the guidance surface operating to aid in the guidance of the at least one medical tool through the opening of the first portion and through the opening of the second movable portion.

2. The medical guidance device of claim 1, wherein:
the second movable portion includes:
a frame defining an opening that operates to overlay the opening of the first portion when the first portion and the second movable portion are mated with each other;
an arc or support member attached to the frame; and
a holder slideably or movably attached to the arc or support member,
wherein the holder operates to hold the at least one medical tool to be guided by the medical guidance device.

3. The medical guidance device of claim 1, wherein one or more of the following:
the first portion includes one or more fiducial markers that operate to align, and confirm alignment of, the first portion that operates to be disposed or positioned on a patient in a targeted orientation or in a predetermined location, over a surgical site;
the medical guidance device operates to be placed or secured onto a patient in the targeted orientation or in the predetermined location, or over the surgical site; and/or
wherein the first portion operates to be fixed to the patient for performing a medical procedure with the at least one medical tool.

4. The medical guidance device of claim 2, wherein one or more of the following:
the holder comprises at least one groove for accepting the at least one medical tool therein;
the at least one medical tool comprises a plurality of medical tools; and/or
the at least one groove of the holder comprises a plurality of grooves where each groove of the plurality of grooves operates to hold a different medical tool of the plurality of medical tools in the respective groove of the plurality of grooves.

5. The medical guidance device of claim 2, wherein the arc or support member includes the guidance surface having the one or more reference marks or the reference scale that operates to aid in the guidance of the at least one medical tool.

6. The medical guidance device of claim 1, wherein one or more of the following:
the first portion and/or the second movable portion includes the one or more illumination or visual indicators on a surface of the first portion or on a surface of the second movable portion, the one or more illumination or visual indicators operating to indicate information to a user of the medical guidance device;
the one or more illumination or visual indicators include two, three, or more illumination or visual indicators; and/or
the information includes one or more of the following: whether one or more guidance features are enabled, whether the one or more guidance features are disabled, a position of the second movable portion, a position of a holder, a position and/or angle of the at least one medical tool, whether the angle of the at least one medical tool is accurately positioned and/or angled or not, whether movement of the second movable portion is accurate or needs adjustment, an insertion plane, different positions and/or angles of the at least one medical tool in a case where the at least one medical tool includes a plurality of medical tools, and/or whether an error has occurred with the medical guidance device.

7. The medical guidance device of claim 6, wherein the one or more illumination or visual indicators include one or more light emitting diodes (LEDs), one or more LED arrays, or one or more lights on the surface of the first portion and/or the second movable portion to indicate the information to the user of the medical guidance device.

8. The medical guidance device of claim 7, wherein the one or more LEDs, the one or more LED arrays, or the one or more lights comprise three LEDs, LED arrays, or lights where a center or middle LED, LED array, or light of the three LEDs, LED arrays, or lights indicates whether the one or more guidance features are enabled or disabled or whether an error has occurred with the medical guidance device, and where the other two LEDs, LED arrays, or lights of the three LEDs, LED arrays, or lights indicate: (i) via flashing, opposite directions in which the medical guidance device should be moved to adjust a guidance angle or direction of the at least one medical tool, (ii) by constantly being on, or by having a green or predetermined color, when to stop making the adjustment(s) to the guidance angle or direction of the at least one medical tool, and (iii) by being off when the one or more guidance features are disabled.

9. The medical guidance device of claim 6, wherein one or more of the following:
one or more of the one or more illumination or visual indicators have different colors; and/or
one or more of the one or more illumination or visual indicators have different shapes.

10. The medical guidance device of claim 6, wherein one or more of the following:
(i) the second movable portion includes:
a frame defining an opening that operates to overlay the opening of the first portion when the first portion and the second movable portion are mated with each other;
an arc or support member attached to the frame; and
a holder slideably or movably attached to the arc or support member, wherein the holder operates to hold the at least one medical tool to be guided by the medical guidance device;

(ii) at least one of the one or more illumination or visual indicators is positioned or disposed on the holder, or on the second movable portion, to indicate whether the holder is accurately positioned or not;

(iii) at least one of the one or more illumination or visual indicators is positioned or disposed on the arc or support member;

(iv) at least one of the one or more illumination or visual indicators is positioned or disposed on the frame;

(v) at least one of the one or more illumination or visual indicators is positioned or disposed on the first portion;

(vi) the arc or support member includes the guidance surface having the one or more reference marks or the reference scale that operates to aid in the guidance of the at least one medical tool; and/or (vii) the first portion, the second movable portion, or the medical guidance device includes one or more auditory signals to indicate some or all of the information to the user of the medical guidance device.

11. The medical guidance device of claim 1,
wherein the first portion operates to be fixed to the patient for performing a medical procedure with the at least one medical tool, and
wherein, in a case where the first portion and the second movable portion are mated together, the encoder sensor operates to achieve the position sensing by detecting position information between the first portion and the second movable portion based on a relative position of the encoder sensor compared with the encoder scale.

12. The medical guidance device of claim 11, wherein one or more of the following:
the encoder sensor faces the encoder scale in the case where the first portion and the second movable portion are mated together;
the encoder scale extends along a predetermined length of one side of the second movable portion; and/or
the encoder scale extends along the entire circumference of the second movable portion around the opening of the second movable portion.

13. The medical guidance device of claim 11, further comprising:
a wireless communication circuit or wireless communicator device that operates to aid the one or more processors in communicating with the another processor wirelessly,
wherein the one or more processors further operate to one or more of the following:
communicate with the encoder sensor and read a position along the encoder scale based on the position of the encoder sensor,
detect any error or errors of the encoder sensor, encoder scale, the one or more processors of the medical guidance device, and/or the medical guidance device, and/or
control the one or more illumination or visual indicators on a surface of the first portion and/or on a surface of the second movable portion to indicate information to a user of the medical guidance device.

14. The medical guidance device of claim 1, wherein
the medical guidance device communicates wirelessly with a first processor of a computer, the computer including the first processor and a first wireless circuit or communicator; and
the medical guidance device further includes a second wireless circuit or communicator that operates to communicate wirelessly with the first wireless circuit or communicator such that the one or more processors operate to communicate with the first processor of the computer via the first and second wireless circuits or communicators, and the encoder sensor operates to detect positional or angular information of the medical guidance device and/or of the at least one medical tool attached to the medical guidance device.

15. The medical guidance device of claim 14, wherein:
the first processor operates to enable one or more guidance features by sending a signal to the one or more processors of the medical guidance device and to disable the one or more guidance features by sending a signal to the one or more processors of the medical guidance device in a case where one or more of the following occur: angle information and a target angle are matched or are substantially the same, angle information is stable, and/or a user aborts the guidance feature or features; and
the one or more processors further operate to one or more of the following:
(i) read angle information and status information from the encoder sensor cyclically,
(ii) transmit the angle information and the status information to the first processor cyclically,
(iii) calculate a difference between each angle information and the target angle during guidance of the at least one medical tool, and/or
(iv) control the one or more illumination or visual indicators on a surface of the first portion and/or on a surface of the second movable portion and/or one or more auditory signals on a surface of the first portion and/or on a surface of the second movable portion to indicate information to a user of the medical guidance device based on the angle information and status information.

16. The medical guidance device of claim 14, wherein:
the first processor operates to enable one or more guidance features by sending a signal to the one or more processors of the medical guidance device; and
the one or more processors further operate to one or more of the following:
(i) read angle information and status information from the encoder sensor cyclically,
(ii) calculate a difference between each angle information and target angle during guidance of the at least one medical tool,
(iii) control the one or more illumination or visual indicators on a surface of the first portion and/or on a surface of the second movable portion and/or one or more auditory signals on a surface of the first portion and/or on a surface of the second movable portion to indicate information to a user of the medical guidance device based on the angle information and status information,
(iv) stop the one or more guidance features in a case where one or more of the following occur: angle information and the target angle are matched or are substantially the same, angle information is stable, and/or a user aborts the guidance feature or features, and/or
(v) send a guidance completion signal to the first processor when the guidance is completed or stopped.

17. A method of guiding at least one medical instrument or tool using a medical guidance device including a first portion including a portion defining an opening and including an encoder sensor, the first portion operating to be fixed to an object, a target, or a patient; a second movable portion that is removably and movably mateable with the first portion, the second movable portion including a portion defining an opening, the second movable portion operating to hold the at least one medical instrument or tool to be guided by the medical guidance device, and the second movable portion including an encoder scale that operates to interact with the encoder sensor to achieve positional sensing between the first portion and the second movable portion; and one or more processors that operate to guide or navigate the at least one medical instrument or tool held in the medical guidance device and that operate to communicate with another processor wirelessly, the method comprising:

mounting the medical guidance device about or over a predetermined insertion point of a surface, the medical guidance device comprising:
positioning the second movable portion to a predetermined position relative to the first portion such that the opening of the first portion overlaps with, is co-planar with, or is parallel to, the opening of the second movable portion and such that the at least one medical instrument or tool operates to pass through the opening of the first portion and the opening of the second movable portion to have access to the object, the target, or the patient;
positioning the at least one medical instrument or tool to a predetermined position upon the second movable portion; and
inserting the at least one medical instrument or tool through the predetermined insertion point,
wherein one or both of the first portion or the second movable portion include one or more of the following:
one or more illumination or visual indicators that operate to aid in the guidance of the at least one medical instrument or tool, and/or
a guidance surface having one or more reference marks or a reference scale, the guidance surface operating to aid in the guidance of the at least one medical instrument or tool through the opening of the first portion and through the opening of the second movable portion.

18. The method of claim 17, wherein:
the second movable portion includes:
a frame defining an opening that operates to overlay the opening of the first portion when the first portion and the second movable portion are mated with each other;
an arc or support member attached to the frame; and
a holder slideably or movably attached to the arc or support member,
wherein the holder operates to hold the at least one medical instrument or tool to be guided by the medical guidance device.

19. The method of claim 17, wherein one or more of the following:
the first portion includes one or more fiducial markers that operate to align, and confirm alignment of, the first portion on a patient in a targeted orientation or in a predetermined location, over a surgical site;
the medical guidance device is placed or secured onto the patient in the targeted orientation or in the predetermined location, or over the surgical site; and/or
wherein the first portion operates to be fixed to the patient for performing a medical procedure with the at least one medical instrument or tool.

20. The method of claim 18, wherein one or more of the following:
the holder comprises at least one groove for accepting the at least one medical instrument or tool therein;
the at least one medical instrument or tool comprises a plurality of medical instruments or tools; and/or
the at least one groove of the holder comprises a plurality of grooves where each groove of the plurality of grooves operates to hold a different medical instrument or tool of the plurality of medical instruments or tools in the respective groove of the plurality of grooves.

21. The method of claim 17, further comprising:
causing a display to display one or more images taken including the at least one medical instrument or tool through the predetermined insertion point and including the medical guidance device;
designating a target position in the displayed image, at which the at least one medical instrument or tool is to be positioned, in response to receiving a user input for selecting a position in the displayed image; and
guiding the at least one medical instrument or tool to or into at least one region of interest.

22. The method of claim 17, further comprising:
enabling one or more guidance features of the medical guidance device using a first processor communicating wirelessly with the one or more processors of the medical guidance device;
having the one or more processors obtain angle information and status information from the encoder sensor of the medical guidance device cyclically;
calculating, via the one or more processors, a difference between each angle information and a target angle during guidance;
sending the angle information and the status information from the one or more processors to the first processor cyclically; and
disabling, via the first processor, the one or more guidance features once guidance is completed or is stopped by sending a signal from the first processor to the one or more processors wirelessly.

23. The method of claim 22, further comprising controlling, via the one or more processors, the one or more illumination or visual indicators on a surface of the first portion and/or on a surface of the second movable portion, one or more auditory signals on a surface of the first portion and/or on a surface of the second movable portion, or one or more light emitting diodes or lights on a surface of the first portion and/or on a surface of the second movable portion that operate to indicate positional information to a user of the medical guidance device based on the calculated difference and the status information.

24. The method of claim 17, further comprising:
enabling one or more guidance features of the medical guidance device using a first processor communicating wirelessly with the one or more processors of the medical guidance device;
having the one or more processors obtain angle information and status information from the encoder sensor of the medical guidance device cyclically;
calculating, via the one or more processors, a difference between each angle information and a target angle during guidance;
stopping or disabling the one or more guidance features of the medical guidance device, via the one or more processors, in a case where one or more of occur: angle information and the target angle are matched or are substantially the same, angle information is stable, and/or a user aborts the guidance feature or features; and sending, via the one or more processors, a guidance completion signal to the first processor when the guidance is completed or stopped.

25. The method of claim 24, further comprising controlling, via the one or more processors, the one or more illumination or visual indicators on a surface of the first portion and/or on a surface of the second movable portion, one or more auditory signals on a surface of the first portion and/or on a surface of the second movable portion, or one or more light emitting diodes or lights on a surface of the first portion and/or on a surface of the second movable portion that operate to indicate positional information to a user of the medical guidance device based on the calculated difference and status information.

26. A medical guidance device comprising:
- a first portion including a portion defining an opening and including an encoder sensor, the first portion operating to be fixed to an object, a target, or a patient;
- a second movable portion that is removably and movably mateable with the first portion, the second movable portion including a portion defining an opening, the second movable portion operating to hold at least one medical tool to be guided by the medical guidance device, and the second movable portion including an encoder scale that operates to interact with the encoder sensor to achieve positional sensing between the first portion and the second movable portion; and
- one or more processors that operate to guide or navigate the at least one medical tool held in the medical guidance device and that operate to communicate with another processor wirelessly,
- wherein the opening of the first portion overlaps with, is co-planar with, or is parallel to, the opening of the second movable portion such that the at least one medical tool operates to pass through the opening of the first portion and the opening of the second movable portion to have access to the object, the target, or the patient, and
- wherein one or both of the first portion or the second movable portion include one or more of the following:
- one or more illumination or visual indicators that operate to aid in the guidance of the at least one medical tool, and/or
- a guidance surface having one or more reference marks or a reference scale, the guidance surface operating to aid in the guidance of the at least one medical tool through the opening of the first portion and through the opening of the second movable portion, wherein one or more of the following:
- the first portion and/or the second movable portion includes the one or more illumination or visual indicators on a surface of the first portion or on a surface of the second movable portion, the one or more illumination or visual indicators operating to indicate information to a user of the medical guidance device;
- the one or more illumination or visual indicators include two, three, or more illumination or visual indicators; and/or
- the information includes one or more of the following: whether one or more guidance features are enabled, whether the one or more guidance features are disabled, a position of the second movable portion, a position and/or angle of the at least one medical tool, whether the angle of the at least one medical tool is accurately positioned and/or angled or not, whether movement of the second movable portion is accurate or needs adjustment, an insertion plane, different positions and/or angles of the at least one medical tool in a case where the at least one medical tool includes a plurality of medical tools, and/or whether an error has occurred with the medical guidance device.

* * * * *